United States Patent [19]

Sprecker et al.

[11] 4,222,941

[45] Sep. 16, 1980

[54] 2-OXABICYCLOOCTANE DERIVATIVES, PROCESSES FOR PREPARING SAME AND ORGANOLEPTIC USES THEREFOR

[75] Inventors: Mark A. Sprecker, Sea Bright; Frederick L. Schmitt, Holmdel; Manfred H. Vock, Locust; Joaquin F. Vinals, Red Bank, all of N.J.; Jacob Kiwala, Brooklyn, N.Y.

[73] Assignee: International Flavors & Fragrances Inc., New York, N.Y.

[21] Appl. No.: 48,752

[22] Filed: Jun. 15, 1979

Related U.S. Application Data

[60] Division of Ser. No. 12,695, Feb. 16, 1979, which is a continuation-in-part of Ser. No. 953,128, Oct. 20, 1978.

[51] Int. Cl.$^3$ ............................................ C07D 309/04
[52] U.S. Cl. ............................ 260/345.1; 252/522 R; 426/536; 568/826
[58] Field of Search ...................................... 260/345.1

[56] References Cited

PUBLICATIONS

The Merck Index, 9th ed., 2280 (1976).

*Primary Examiner*—Nicky Chan
*Attorney, Agent, or Firm*—Arthur L. Liberman

[57] ABSTRACT

Described are derivatives of 2-oxabicyclo[2.2.2]octanes and precursors therefor, cyclohexenemethanols as well as organometallic salts of said cyclohexenemethanols. The oxabicyclooctanes are useful in perfumery and foodstuff and medicinal product flavors. The cyclohexenemethanols and their oganometallic salts are useful as precursors for the oxabicyclooctanes.

7 Claims, 21 Drawing Figures

GLC PROFILE FOR EXAMPLE II.

GLC PROFILE FOR EXAMPLE I.

NMR SPECTRUM FOR EXAMPLE I.

IR SPECTRUM FOR EXAMPLE I

NMR SPECTRUM FOR EXAMPLE II, FRACTION 10.

IR SPECTRUM FOR EXAMPLE II, FRACTION 10.

GLC PROFILE FOR EXAMPLE III.

PRODUCT

NMR SPECTRUM FOR EXAMPLE III, FRACTION 10.

IR SPECTRUM FOR EXAMPLE III, FRACTION 10.

GLC PROFILE (AFTER 8 Hr. REFLUXING) FOR EXAMPLE IV.

NMR SPECTRUM FOR EXAMPLE IV, FRACTION 10.

IR SPECTRUM FOR EXAMPLE IV, FRACTION 10.

GLC PROFILE, EXAMPLE V

PRODUCT

NMR SPECTRUM FOR EXAMPLE V, FRACTION 7.

IR SPECTRUM FOR EXAMPLE V, FRACTION 7.

GLC PROFILE FOR EXAMPLE VI

GLC PROFILE FOR EXAMPLE VII.

NMR SPECTRUM FOR EXAMPLE VI, FRACTION 8.

IR SPECTRUM FOR EXAMPLE VI, FRACTION 8.

NMR SPECTRUM FOR EXAMPLE VII, FRACTION 5.

IR SPECTRUM FOR EXAMPLE VII, FRACTION 5.

2-OXABICYCLOOCTANE DERIVATIVES, PROCESSES FOR PREPARING SAME AND ORGANOLEPTIC USES THEREFOR

This is a divisional of application Ser. No. 012,695, filed 2/16/79 which in turn is a continuation-in-part of U.S. Letters Pat., Ser. No. 953,128 filed on 10/20/78.

BACKGROUND OF THE INVENTION

The instant invention provides novel oxabicyclooctanes having the structure:

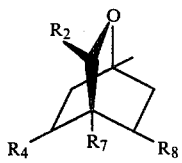

wherein $R_2$ is one of $C_2-C_5$ alkyl or alkenyl; $R_4$ is hydrogen, methyl or ethyl, $R_7$ is hydrogen or methyl; and $R_8$ is hydrogen or methyl as well as intermediates for producing same having the generic structure:

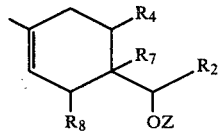

wherein $R_2$, $R_4$, $R_7$ and $R_8$ are defined as above and wherein Z is hydrogen or MgX and wherein X is chloro, bromo or iodo, and also provides uses of said novel oxabicyclooctanes for their organoleptic properties in consumable materials.

Chemical compounds which can provide dry woody (sandalwood), leathery, fruity, cineol/camphoraceous, piney, anise-like, spicey, green, earthy, minty and etherial aromas with chocolate-like backgrounds and ether/clove notes are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

By the same token, materials which can provide eucalyptus-like, herbacious, blueberry-like, piney, lime-like, clove, banana-like, woody, oriental-like, spicey, black pepper and floral aromas and eucalyptus, herbacious-like, blueberry-like, piney, lime-like, tangarine-like, clove, banana-like, woody, oriental-like, spicey, black pepper-like and floral flavor characteristics with a stringent, biting and bitter effects are desirable in applying the art of flavoring to foodstuffs, toothpastes, chewing gums and medicinal products. Many of the natural materials which provide such flavor notes and contribute desired nuances to flavoring compositions are high in cost, vary in quality from one batch to another and/or are generally subject to the usual variations of natural products.

There is, accordingly, a continuing effort to find synthetic materials which will replace, enhance or augment the essential flavor and fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined clove, banana or spice flavor, has been difficult and relatively costly in the areas of both natural products and synthetic products.

Artificial flavoring agents for foodstuffs have received increasing attention in recent years. For many years, such food flavoring agents have been preferred over natural flavoring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums and toothpastes is not completely known. This is noticeable in products having mint, lime, clove bud-like, banana and spice flavor characteristics, particularly.

Even more desirable are products that can serve to substitute for difficult-to-obtain natural perfumery oils and at the same time substitute for natural flavoring ingredients in foodstuffs, chewing gums, medicinal products and toothpastes and in addition, at the same time, substitute for natural flavoring ingredients in tobaccos. The compounds of this invention are versatile in such a way as to be of such use.

Arctander in "Perfume and Flavor Chemicals (Aroma Chemicals)", Vol. I, 1969 at monograph No. 616 describes 1,8-cineole having the structure:

as being useful in perfumery and flavor compositions. Thus, Arctander states, regarding 1,8-cineole:

"Fresh, diffusive, camphoraceous-cool odor of poor tenacity. Sweet and fresh, cool-camphoraceous taste and cool mouthfeel unless very highly concentrated.

Widely used in perfume compositions for its refreshing effect in herbaceous type fragrances, Lavender, New Mown Hay, Fougere, etc. and in medicinal type odors for soap and household products. Also, in making odors for industrial purposes, unless Eucalyptus oil must be used for its lower cost.

This oxide has found increased usage during the 1965/66 period of abnormally high prices for Lavandin and Spike Lavender oils.

The odor of Eucalyptus is, in some countries, rated synonomous with masking odors for lavatories, etc., a fact which has an unquestionable psychological effect, causing people to reject the odor of Eucalyptus for oral-hygienic purposes, etc. Similar viewpoints has been observed about the use of Methylsalicylate in dentifrice in many European countries. Peculiarly enough, Methylsalicylate is still a popular candy-, soft-drink- and toothpaste flavor in the U.S.A., where the ester at the same time is used as a masking agent in toilet-bowl cleaners!

The 'olfactory association' is quite human and common, but it may at times completely destroy the changes of a chemical from its use in flavors or other field.

Eucalyptol is extensively used in flavor compositions, particularly in all types of preparations for oral hygiene, dentifrice, breath-sprays, mouthwashes, cough lozenges, pastilles, skin-rubbing lotions, inhalator fluids, etc.

It seem, however, that its use in skin rubbing lotions has hampered its popularity as a candy flavor in the U.S.A.

Normal use concentrations are about 1 to 15 ppm in the finished (flavored) product, but concentrations as high as 200 ppm are found in chewing gum."

Furthermore, the compound having the structure:

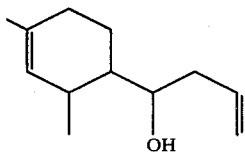

and the compound having the structure:

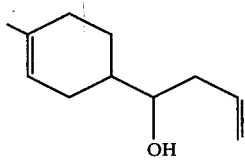

are reported by Sopov and Kovner at Zh. Obsch. Khim. 34, 1492-6 (1964) as abstracted in Chem. Abstracts, Vol. 61, 5529b.

The Sopov and Kovner reference does not, however, disclose organoleptic uses of the compounds having the structures:

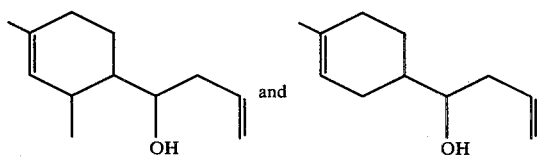

Furthermore, nothing in the prior art discloses any of the compound the generic structure:

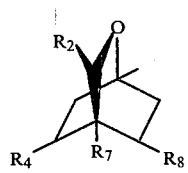

wherein $R_2$ is $C_2$-$C_5$ alkyl or alkenyl; $R_4$ is methy, ethyl or hydrogen; $R_7$ is methyl or hydrogen and $R_8$ is methyl or hydrogen; and nothing in the prior art discloses organoleptic uses or uses as intermediates of the compounds having the generic structure:

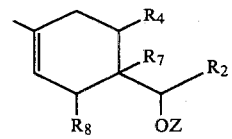

wherein Z is hydrogen or MgX and wherein X is chloro, bromo or iodo.

Insofar as their organoleptic uses are concerned, the compounds of the instant invention have unexpected, unobvious and advantageous properties over such compounds of the prior art as 1,8-cineole.

THE INVENTION

Figure 4:
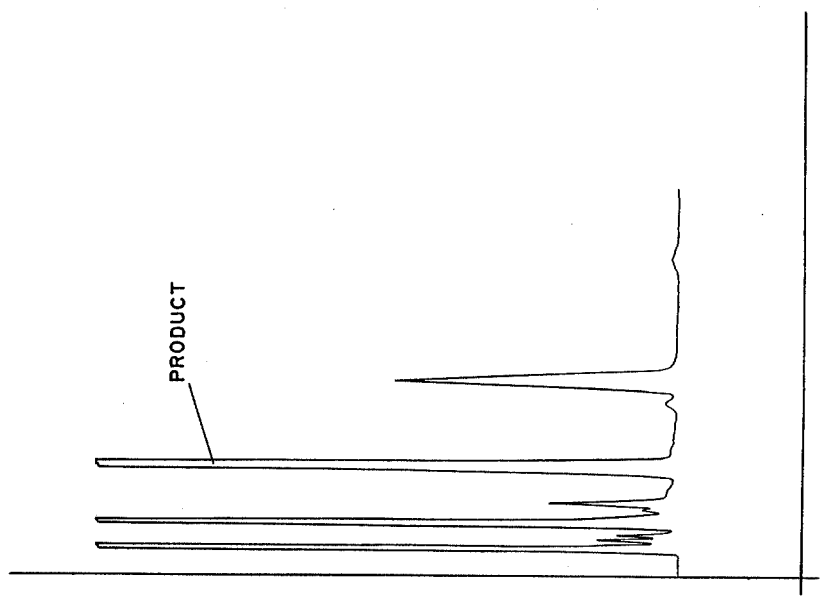
FIG. 4 is the GLC profile for the product produced according to Example II, 1,4-dimethyl-3-n-butyl-2-oxabicyclo[2.2.2]octane.

It has now been determined that certain oxabicyclooctanes are capable of imparting a variety of flavors and fragrances to various consumable materials and are also capable of augmenting or enhancing a variety of flavors and fragrances of various consumable materials.

Briefly, our invention contemplates augmenting or enhancing the flavors and/or fragrances of such consumable materials as perfues, perfumed articles, colognes, foodstuffs, chewing gums, toothpastes, medicinal products and smoking tobaccos by adding thereto a small but effective amount of at least one of the compound having the generic structure:

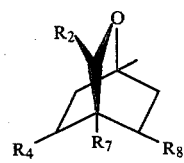

wherein $R_2$ is $C_2$-$C_5$ alkyl or alkenyl; $R_4$ is hydrogen, methyl or ethyl; $R_7$ is hydrogen or methyl; and $R_8$ is hydrogen or methyl with the proviso that at least two of $R_4$, $R_7$ and $R_8$ are not hydrogen.

Also contemplated within the scope of our invention are intermediates for producing such oxabicyclooctanes which intermediates having the generic structure:

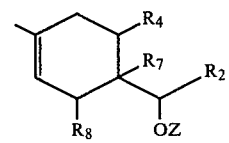

wherein $R_2$, $R_4$, $R_7$ and $R_8$ are as defined above and Z is hydrogen or MgX and wherein X is chloro, bromo or iodo.

The oxabicyclooctane derivatives of our invention augment or enhance eucalyptus, herbaceous, blueberry-like, piney, lime-like, clove, banana-like, woody, oriental-like, spicey, black pepper, and floral aroma characteristics and eucalyptus, herbaceous, blueberry-like, piney, lime-like, tangerine-like, clove bud-like, banana-like, woody, oriental-like, spicey, black pepper and floral flavor characteristics with a stringent, biting and bitter effects insofar as augmenting or enhancing the aroma or taste of foodstuffs, toothpastes, medicinal products and chewing gums.

The oxabicyclooctane derivatives of our invention also augment or enhance the dry woody (sandalwood), leathery, fruity, cinceol/camphoraceous, piney, anise-like, spicey, green, earthy, minty and ether/clove aromas of perfumes, perfumed articles and colognes of our invention.

The oxabicyclooctane derivatives of our invention also augment or enhance the clove bud-like characteristics of smoking tobacco by imparting thereto a clove bud aroma and taste nuance prior to and on smoking in the main stream and in the side stream.

Examples of the oxabicyclooctane derivatives of our invention and their organoleptic characteristics are as follows:

| STRUCTURE OF COMPOUND | NAME OF COMPOUND | FLAVOR CHARACTERISTICS | FRAGRANCE CHARACTERISTICS |
|---|---|---|---|
|  | 3-ethyl-1,5,8-trimethyl-2-oxabicyclo[2.2.2]octane | A eucalyptus, herbaceous, blueberry-like, piney and lime-like aroma character with a eucalyptus, herbaceous, blueberry, piney, lime, tangerine flavor characteristics with astringent nuances at 5ppm. | A green, earthy, minty aroma with spicey, hazel-like nuances. |
|  | 3-isopropyl-1,5,8-trimethyl-2-oxabicyclo[2.2.2]octane | A clove, herbaceous, banana-like and woody aroma characteristic with a clove, herbaceous, banana and woody flavor characteristic and biting effect at 5ppm. | An etherial, minty, medicinal aroma with ether/clove nuances. |
|  | 3-n-butyl-1,5,8-trimethyl-2-oxabicyclo[2.2.2]octane | A herbaceous, eucalyptus-like, piney aroma with a herbaceous, eucalyptus and piney flavor profile with bitter characteristics at 2ppm. | A dry woody (sandalwood), leathery natural-like aroma. |
|  | 3-isopropyl-1,4-dimethyl-2-oxabicyclo[2.2.2]octane | A herbaceous, eucalyptus, oriental-like aroma with a herbaceous, eucalyptus-like, oriental flavor profile and bitter characteristics at 20ppm. | A fruity cineol/camphoraceous pine aroma. |

| STRUCTURE OF COMPOUND | NAME OF COMPOUND | FLAVOR CHARACTERISTICS | FRAGRANCE CHARACTERISTICS |
|---|---|---|---|
| | 3-n-butyl-1,4-dimethyl-2-oxabicyclo[2.2.2]octane | A herbaceous, spicey, black pepper-like, floral aroma with a herbaceous, spicey, black pepper-like and floral flavor characteristic in bitter nuances at 10 ppm. | An anise-like spicey medicinal aroma with chocolate-like undertones. |

The oxabicyclooctane derivatives and the cylohexene alkyl and alkenyl carbinols of our invention can be produced by first forming a cyclohexene carboxaldehyde by reaction of an alpha,beta-unsaturated aldehyde with a conjugated diene. The resulting cyclohexene carboxaldehyde is then reacted with a Grignard reagent to form an organometallic salt of a cyclohexene carbinol. The organometallic salt of the cyclohexene carbinol is then hydrolyzed (in the presence of acid) to form a cyclohexene carbinol of our invention. This reaction product is then further reacted by cyclizing the compound to form the desired 2-oxabicyclo[2,2,2]octane. The over-all reaction sequence described above is as follows:

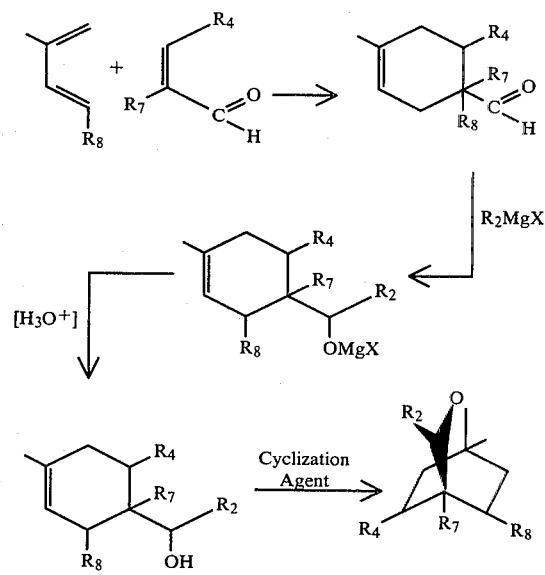

wherein $R_2$ is $C_2$–$C_5$ alkyl or alkenyl; $R_4$ is hydrogen, methyl or ethyl, $R_7$ is hydrogen or methyl; and $R_8$ is hydrogen or methyl with the proviso that when $R_4$ is methyl or ethyl, $R_7$ and $R_8$ are not both hydrogen and that at least one of $R_7$ and $R_8$ is methyl. In addition, X is chloro, bromo or iodo.

The Diels-Alder reaction of the alpha,beta-unsaturated aldehyde with the conjugated diene is a procedure well known in the prior art. The reaction may be carried out in the presence of Lewis acid catalysts such as zinc chloride, aluminum chloride or aluminum bromide; or it may be carried out in the absence of catalysts at higher temperatures, e.g., 50° C. up to 150° C. When carrying out the Diels-Alder reaction in the presence of catalysts, lower temperatures, e.g., −10° C. up to 30° C. may be utilized.

That part of the reaction sequence whereby the cyclohexene carboxaldehyde is reacted with the Grignard reagent to form the cyclohexene carbinol organometallic salt followed by hydrolysis of the cyclohexene carbinol organometallic salt to form the cyclohexene carbinol followed by cyclization of the resulting cyclohexene carbinol to form the 2-oxabicyclo[2,2,2]octane may be carried out either in one step or in two steps.

In carrying out the "two-step reaction" whereby the cyclohexene carbinol is first isolated and then cyclized in the first step, that is, in the reaction of the Grignard reagent with the cyclohexene carboxaldehyde, the mole ratio of alkyl halide or alkenyl halide to magnesium in order to form the Grignard reagent is from 0.9:1 up to 1.5:1. The mole ratio of alkyl halide or alkenyl halide to cyclohexene carboxaldehyde is from 0.8:1 up to 1.5:1. This reaction of the Grignard reagent with the cyclohexene carboxaldehyde takes place in an ether solvent such as diethyl ether, tetrahydroduran or di-n-butyl ether or another inert solvent such as toluene, chloroform or benzene to which two equivalents of ether has been added. The temperature of reaction preferably is between 0° and 100° C. with the most preferred temperature range for this reaction being from 35° C. up to 45° C.

In the two-step reaction, the resulting cyclohexene carbinol is then isolated as by distillation. The resulting cyclohexene carbinol is then cyclized at a temperature in the range of from 25° C. up to 150° C. in the presence of an acid such as aqueous hydrochloric acid or sulfuric acid or phosphoric acid. This acid may be used in combination with an alcohol such as isopropyl alcohol or with some other solvents such as tetrahydrofuran or acrylonitrile or the acid may be used by itself to effect the cyclization. The cyclization in the alternative may be carried out using a Lewis Acid such as borontrifluoride, aluminum trichloride, zinc chloride, stannic chloride or zinc bromide in the presence of a solvent such as toluene, chloroform or xylene.

As stated above, the reaction of the cyclohexene carboxaldehyde to form the cyclohexene carbinol followed by cyclization may take place in a single reactor without separation of the cyclohexene carbinol. The conditions are the same as stated above for the two-step reaction.

The oxabicyclooctane derivatives of our invention can be obtained in pure form or in substantially pure form by conventional purification techniques. Thus, the products can be purified and/or isolated by distillation, extraction, crystallization, preparative chromatographic techniques (column chromatography and vapor phase chromatography) and the like. It has been found desirable to purify the oxacyclooctane derivatives of our invention by fractional distillation in vacuo.

When the oxabicyclooctane derivatives of our invention are used as food flavor adjuvants, the nature of the co-ingredients included with said oxabicyclooctane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks, and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine, and a flavoring composition which incorporates one or more of the oxabicyclooctane derivatives of our invention, and in addition, sweetening agents which may be sugars, including sucrose or dextrose and/or artificial sweeteners such as cyclamates or saccharin. Other optional ingredients may also be present.

Substances suitable for use hereinas co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising, broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anti-caking agents, e.g., aluminum calcium sulfate and tri-basic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, proprionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-diemthyl acrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alphaphellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as $\gamma$-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatible with the oxabicyclooctane derivatives of our invention by not covering or spoiling the organoleptic properties (aroma and/or taste) thereof; (ii) be non-reactive with the oxabicyclooctene derivatives of our invention and (iii) be capable of providing an environment in which the oxabicyclooctane derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of oxabicyclooctane derivatives employed in a particular instance can vary over a relatively wide range, depending upon the desired organoleptic effects to be achieved. Thus, correspondingly, greater amounts would be necessary in those instances wherein the ultimate food composition to be flavored (e.g., with a blueberry flavor or a clove bud oil-like flavor) is relatively gland to the taste, whereas relatively minor quantities may suffice for purposes of enhancing the composition merely deficient in natural flavor or aroma. The primary requirement is that the amount selected by effective, i.e., sufficient to alter, modify, or enhance the organoleptic characteristics of the parent composition, whether foodstuff per se, chewing gum per se, medicinal product per se, toothpaste per se, or flavoring composition.

The use of insufficient quantities of oxabicyclooctane derivatives will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent wth the obtention of desired flavoring effects.

Thus, and with respect to ultimate food compositions, chewing gum compositions, medicinal product compositions and toothpaste compositions, it is found that quantities of bicyclooctane derivatives ranging from a small but effective amount, e.g., 0.05 parts per million up to about 500 parts per million based on total composition, are suitable. Concentrations in excess of the maximum quantity stated are not normally recommended since they fail to provide commensurate enhancement of organoleptic properties. In those instances wherein the bicyclooctane derivatives are added to the foodstuff as an integral component of a flavoring composition, it is of course, essential that the total quantity of flavoring composition employed be sufficient to yield an effective bicyclooctane derivative concentration in the foodstuff product.

Food flavoring compositions prepared in accordance with the present invention preferably contain the bicyclooctane derivatives in concentrations ranging from about 0.025% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the bicyclooctane derivatives with, for examples, gum arabic, gum tragacanth, carrageenan and the like, and thereafter spray-drying the resultant mixture whereby to obtain the particular solid product. Preprepared flavor mixes in powder form, e.g., a fruit-flavored powder mix, are obtained by mixing the dried solid components, e.g., starch, sugar and the like, and bicyclooctane derivatives in a dry blender until the requisite degree of uniformity is achieved.

It is presently preferred to combine with the bicyclooctane derivatives of our invention, the following adjuvants: Oil of Cubeb; Phellandrene; beta-Phellandrene; Oil of Coriander; Pil of Pimento Leaf, Oil of Patchouli; Natural Lemon Oil; Acetaldehyde; Alpha-Terpineol; Citral; Carvone; Terpinolene; Alpha-Terpinene; Diphenyl; Alpha-Fenchyl Alcohol; Cineole; Limonene; Linalool; Geranyl Acetate; Nootkatone; Neryl Acetate; Heliotropin; Maltol; Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine, Piperidine; Pil of Black Pepper; Black Pepper Oleoresen; Capsicum; Oil of Nutmeg; Cardamon Oil; Clove Oil; Separmint Oil; Oil of Peppermint; and $C_{10}$-Terpinyl Ethers as described in Application for U.S. Pat. Ser. No. 872,937 filed on Jan. 27, 1978, now U.S. Pat. No. 4,131,687 issued on Dec. 26, 1978 (such as fenchyl ethyl ethers).

The oxabicyclooctane derivatives of our invention can be used to contribute dry woody (sandalwood), leather, fruity, cineol/camphoraceous, piney, anise-like, spicey, green, earthy, minty, etherial aromas with chocolate-like and ether/clove undertones to perfumes, perfumed articles and colognes. As olfactory agents, the oxabicyclooctane derivatives and the cyclohexene alkyl and alkenyl carbinols and esters of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundations tone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the oxabicyclooctane derivatives of this invention which will be effective in perfume compositions depends on many factors, including the other ingredients, their amounts and the effects which are desired. It has been found that perfume compositions containing as little as 0.5% of the oxabicyclooctane derivatives of this invention, or even less, can be used to impart an interesting minty, herbaceous and/or anise-like aroma to soaps, liquid and solid cationic, anionic and nonionic detergents, cosmetics, powders, liquid and solid fabric softeners, optical brightener compositions, and other products. The amount employed can range up to 50% or higher and will depend on considerations of cost, nature of the end product, and the effect desired on the finished product and particular fragrance sought.

The oxabicyclooctane derivatives of this invention can be used alone or in a perfume composition as an olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01% of one or more of the oxabicyclooctane derivatives will suffice to impart an interesting dry woody (sandalwood), leathery, fruity, cineol/camphoraceous, piney, anise-like, spicey, green, earthy, minty, etherial and/or clove bud-like aroma. Generally, no more than 0.5% is required.

In addition, the perfume composition can contain a vehicle or carrier for the oxabicyclooctane derivatives alone or with other ingredients. The vehicle can be a liquid such as an alcohol such as ethanol, a glycol such as propylene glycol, or the like. The carrier can be an absorbent solid such as a gum or components for encapsulating the composition such as gelatin which can be used to form a capsule wall surrounding the perfume oil as by means of coacervation.

An additional aspect of our invention provides an organoleptically improved smoking tobacco product and additives therefor including methods of making the same which overcome problems heretofore encountered in the creation or enhancement of specific desired clove bud-like notes. Such noted, both prior to and on smoking, in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable clove bud-like notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the oxabicyclooctane derivatives of our invention.

In addition to the oxabicyclooctane derivatives of our invention, other flavoring and aroma additives may be added to the smoking tobacco material or substitute therefor either separately or in mixture with one or more of the oxabicyclooctane derivatives of our invention:

I. Synthetic Materials
Beta-methylcinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl-5-isopropylacetophenone;
2-Hydroxy-2,5,5,8α-tetramethyl-1-)2-hydroxyethyl)-decahydronaphthalene;
Dodecahydro-3α,6,6,9α-tetramethylnaphtho(2,1-β)-furan;
4-Hydroxyhexenoic acid, gamma-lactone;
Polyisoprenoid hydrocarbons defined in Example V of U.S. Pat. No. 3,589,372 issued on June 29, 1971

II. Natural Oils
Celery seed oil;
Coffee extract;
Bergamot oil;
Cocoa extract;
Nutmeg oil;
Origanum oil.

An aroma and flavoring concentrate containing one or more of the oxabicyclooctane derivatives of our invention and, if desired, one or more of the above-indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of clove bud-like notes prior to and on smoking, in both the main stream and the side stream, we have found that satisfactory results are obtained if the proportion by weight of the sum total of oxabicyclooctane derivatives to smoking tobacco material is between 50 ppm and 1500 ppm (0.005%–0.15%) of the active ingredients to the smoking tobacco material. We have further found that satisfactory results are obtained if the proportions by weight of the sum total of oxabicyclooctane derivatives used to flavoring material is between 0.05:1 and 0.50:1.

Any convenient method for incorporating the oxabicyclooctane derivatives in the tobacco product may be employed. Thus the oxabicyclooctane derivatives taken alone or along with other flavoring additives may be dissolved in a suitable solvent such as food grade ethanol, pentane, diethyl ether and/or other volatile organic solvents, and the resulting solution may either be sprayed on the cured, cased and blended tobacco material; or the tobacco material or filter may be dipped into such solution. Under certain circumstances, a solution of one or more oxabicyclooctane derivatives taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have one or more oxabicyclooctane derivatives of our invention in excess of the amounts or concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated supra, the oxabicyclooctane derivatives of our invention can be incorporated with materials such as filter tip materials, seam paste, packaging materials and the like which are used along with the tobacco to form a product adapted for smoking. Futhermore, the oxabicyclooctane derivatives of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that the oxabicyclooctane derivatives of our invention can be utilized to alter, modify, augment or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

Preparation of 3-Ethyl-1,5,8-Trimethyl-2-Oxabicyclo[2.2.2]Octane

Reaction:

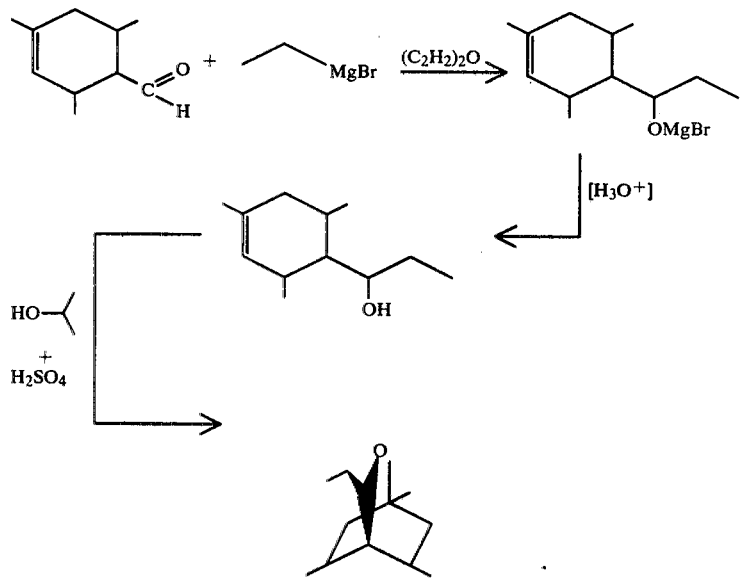

A solution of ethyl magnesium bromide in ether is prepared by dropwise adding a solution of 379.5 grams (3.45 moles) of ethyl bromide in 700 mls of dry ether to a stirred slurry of 76.5 grams of magnesium (3.15 moles) in 600 mls of dry ether under nitrogen at reflux. The resulting solution is stirred at reflux for 30 minutes. A solution of 444 grams of 2,4,6-trimethyl-3-cyclohexenylcarboxaldehyde (3.0 moles) in 200 mls of ether is then added to the reaction mixture over a period of 1 hour at reflux under nitrogen. The resulting slurry is heated at reflux for 30 minutes and then cooled to 0° C. 1200 grams of 20% (wt/wt) sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 300 grams of isopropyl alcohol is added to the reaction mixture. Sulfuric acid (100 grams) is added slowly and the resulting solution is heated to reflux for 9 hours. At the end of this period the reaction mass is cooled. 500 ml of water and 200 ml of toluene is added thereto with stirring. The phases are allowed to separate and the aqueous phase is discarded. The organic phase is washed twice with H$_2$O, with sufficient sodium carbonate added to the second wash to adjust to pH to 7-8. Distillation of the organic layer affords 290 grams of 3-ethyl-1,5,8-trimethyl-2-oxabicyclo[2.2.2]octane. (b.p. 90° C., 60mm)

The NMR and IR spectra show fraction 6 of the distillation.

Figure 1:
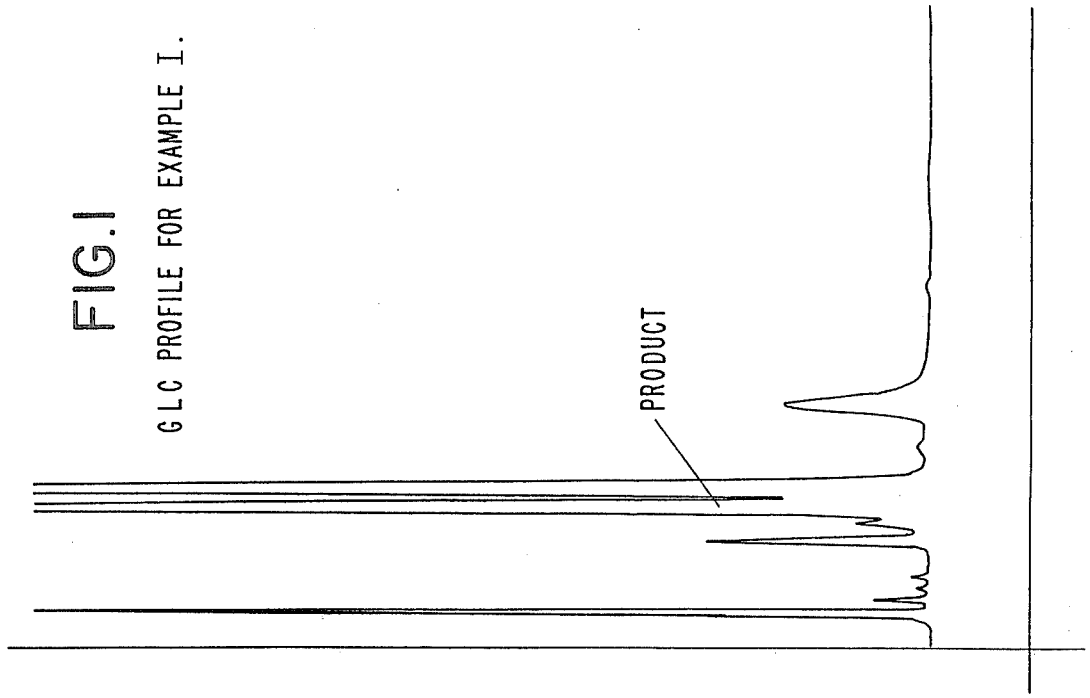
FIG. 1 is the GLC profile for the product produced according to Example I, 3-ethyl-1,5,8-trimethyl-2-oxabicyclo[2.2.2]octane.
Figure 2:
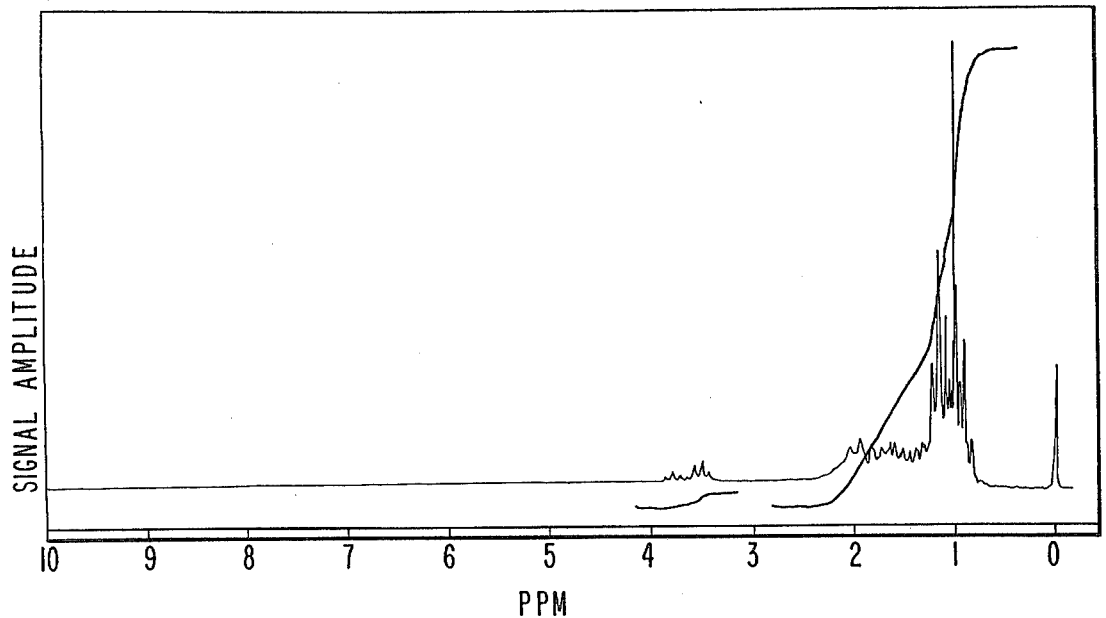
FIG. 2 is the NMR spectrum for the product produced according to Example I.
Figure 3:
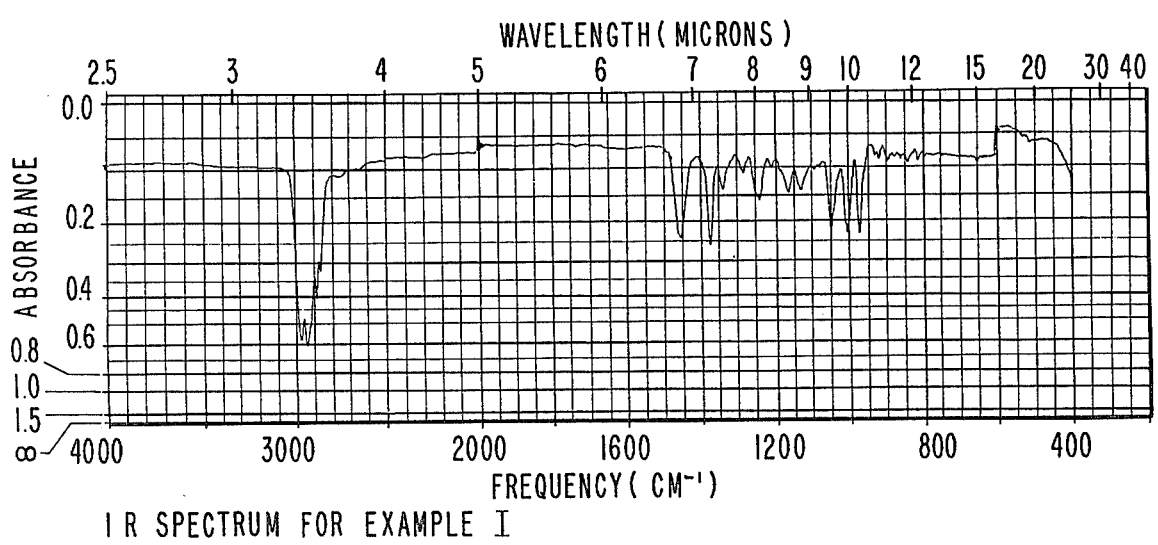
FIG. 3 is the infra-red spectrum for the product produced according to Example I.

FIG. 1 is the GLC profile for the reaction product (Conditions: 180° isothermal; SE-30 column). The NMR spectrum for the resulting reaction product is set forth in FIG. 2. The infra-red spectrum for the resulting reaction product is set forth in FIG. 3.

EXAMPLE II

Preparation of
3-n-Butyl-1,4-Dimethyl-2-Oxabicyclo[2.2.2]Octane
Reaction:

reflux for 30 minutes and then cooled to 0° C. 1200 grams of 20% wt/wt sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 300 grams of isopropyl alcohol is added to the reaction mixture. Sulfuric acid (100 grams) is added slowly and the resulting solution is heated to reflux for 6 hours. At the end of this period the reaction mass is cooled. 500 ml of water and 200 ml of toluene is added thereto with stirring. The phases are allowed to separate and the aqueous phase is discarded. The organic phase is washed twice with H$_2$O, with sufficient sodium carbonate added to the second wash to adjust to pH to 7-8. Distillation of the organic layer afford 169 grams of product (b.p. 65°, 2.5 mm).

The NMR and IR spectra show fraction 10 of the distillation.

FIG. 4 is the GLC profile for the reaction product

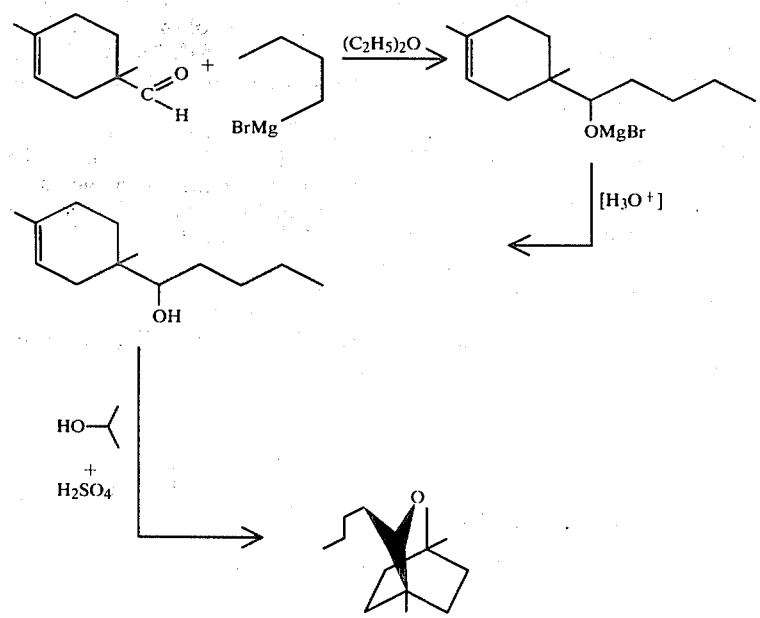

Figure 5:
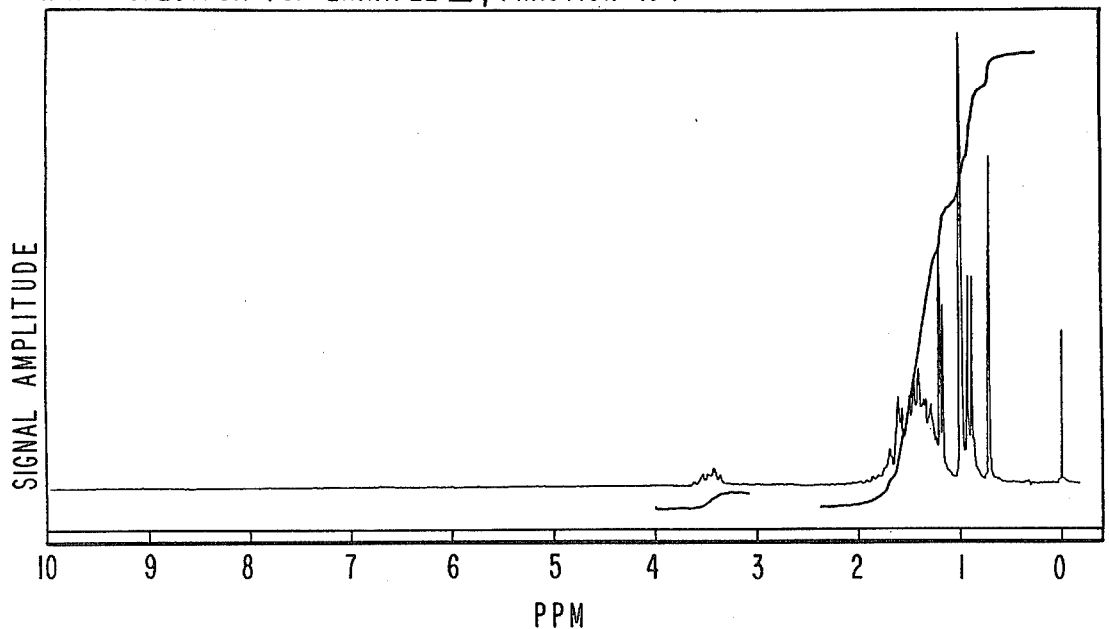
FIG. 5 is the NMR spectrum for fraction 10 of the distillation product produced according to Example II.
Figure 6:
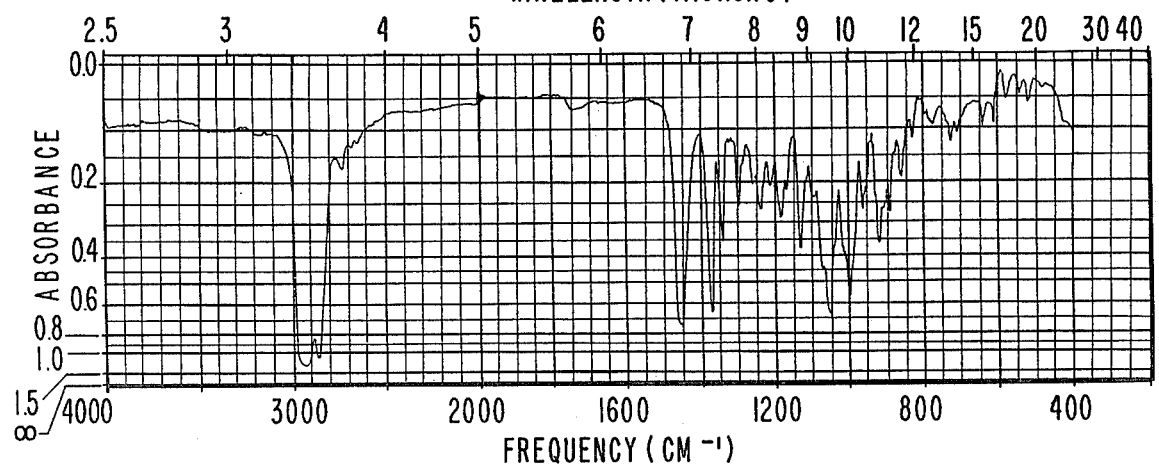
FIG. 6 is the infra-red spectrum for fraction 10 of the distillation product produced according to Example II.

A solution of n-butylmagnesium bromide in ether is prepared by dropwise adding a solution of 138 grams (3.3 moles) of 1-bromobutane in 600 mls of dry ether to a stirred slurry of 76.5 grams of magnesium (3.15 moles) in 700 mls of dry ether under nitrogen at reflux. The resulting solution is stirred at reflux for 30 minutes. A solution of 420 grams of 1,4-dimethyl-3-cyclohexenyl-carboxaldehyde (3.0 moles) in 200 mls of ether is then added to the reaction mixture over a period of 1 hour at reflux under nitrogen. The resulting mixture is heated at (Conditions: 180° isothermal; SE-30 column). The NMR spectrum for the resulting reaction product is set forth in FIG. 5. The infra-red spectrum for the resulting reaction product is set forth in FIG. 6.

EXAMPLE III

Preparation of
3-Isopropyl-1,5-Dimethyl-2-Oxabicyclo[2.2.2]Octane
Reaction:

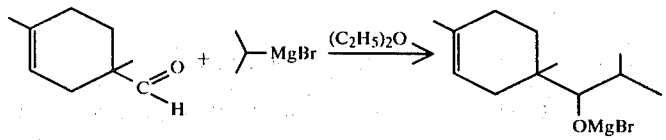

-continued

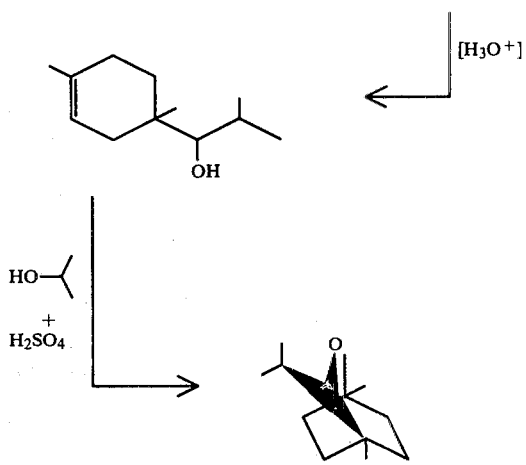

A solution of isopropyl magnesium chloride in ether is prepared by dropwise adding a solution of 259 grams (3.3 moles) of 2-chloropropane in 600 mls of dry ether to a stirred slurry of 76.5 grams of magnesium (3.15 moles) in 700 mls of dry ether under nitrogen at reflux. The resulting solution is stirred at reflux for 30 minutes. A solution of 420 grams of 1,4-dimethyl-3-cyclohexenylcarboxaldehyde (3.0 moles) in 200 ml of ether is then added to the reaction mixture over a period of 1 hour at reflux under nitrogen. The resulting slurry is heated at reflux for 30 minutes and then cooled to 0° C. 1200 grams of 20% wt/wt sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 300 grams of isopropyl alcohol is added to the reaction mixture. Sulfuric acid (100 grams) is added slowly and the resulting solution is heated to reflux for 8 hours. At the end of this period the reaction mass is cooled. 500 ml of water and 200 ml of toluene is added thereto with stirring. The phases are allowed to separate and the aqueous phase is discarded. The organic phase is washed twice with $H_2O$, with sufficient sodium carbonate added to the second wash to adjust to pH to 7-8. Distillation of the organic layer affords 240 gram of product. (b.p. 51°, 2.0mm).

The NMR and IR spectra show fraction 10 of the distillation.

Figure 7:
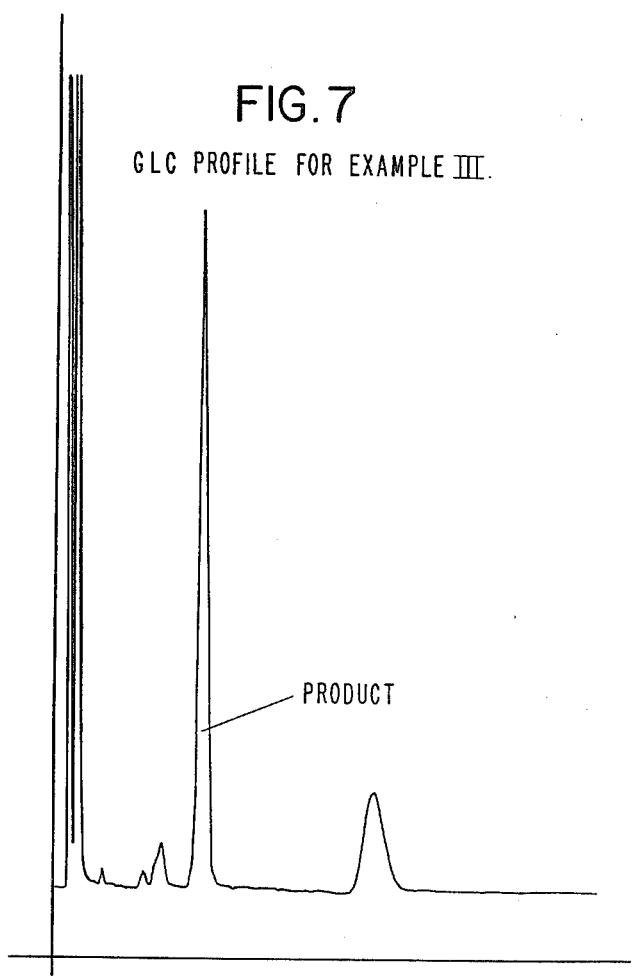
FIG. 7 is the GLC profile for the product produced according to Example III, 1,4-dimethyl-3-i-propyl-2-oxabicyclo[2.2.2]octane.
Figure 8:
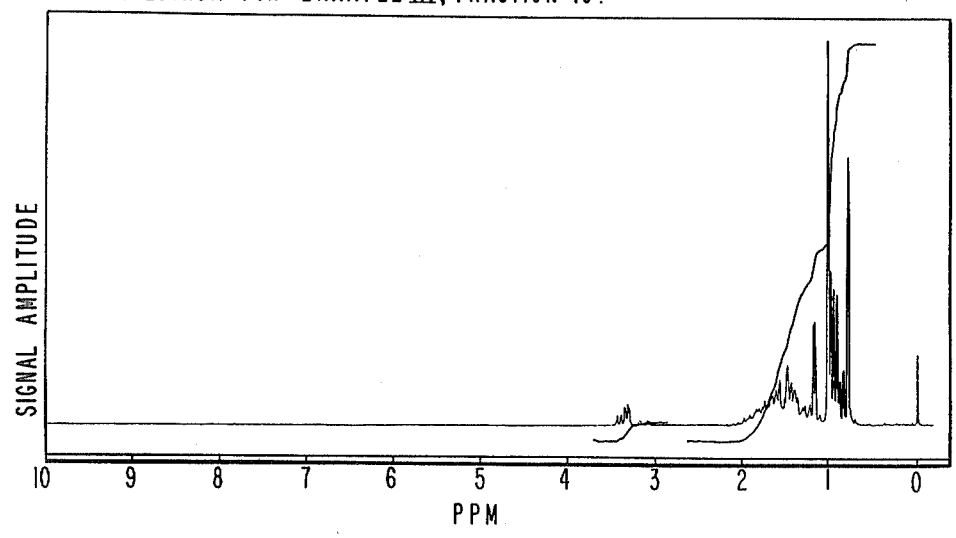
FIG. 8 is the NMR spectrum for fraction 10 of the disillate of the product produced according to Example III.
Figure 9:
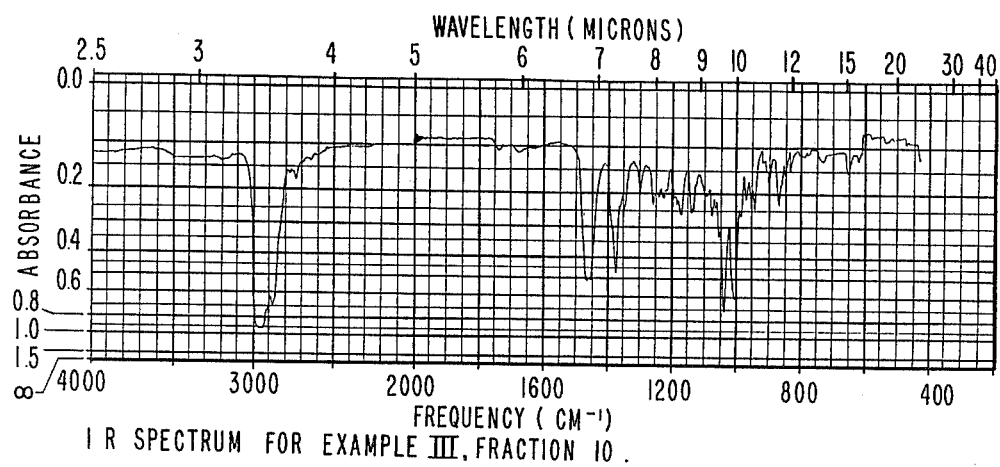
FIG. 9 is the infra-red spectrum for fraction 10 of the distillate of the product produced according to Example III.

FIG. 7 is the GLC profile for the reaction product (Conditions: 180° isothermal; SE-30 column). The NMR spectrum for the resulting reaction product is set forth in FIG. 8. The infra-red spectrum for the resulting reaction product is set forth in FIG. 9.

EXAMPLE IV

Preparation of
3-n-Butyl-1,5,8-Trimethyl-2-Oxabicyclo[2.2.2]Octane
Reaction:

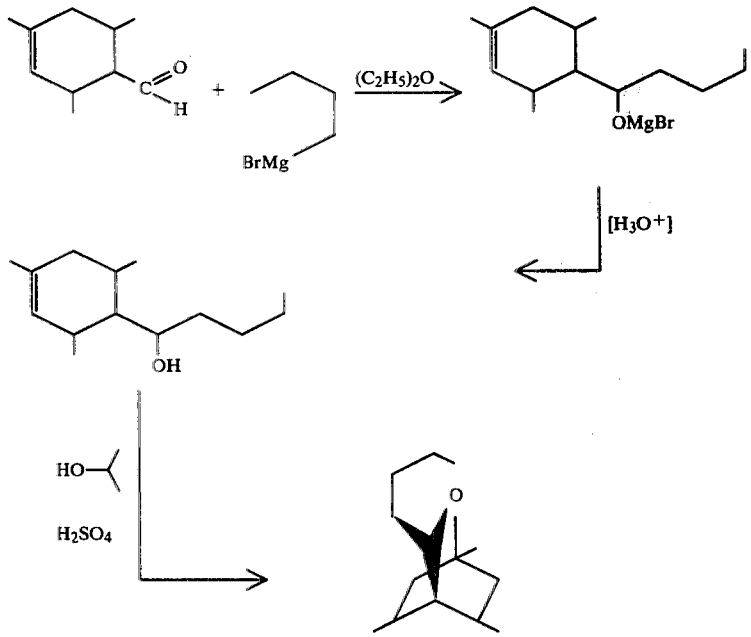

A solution of butylmagnesium bromide in ether is prepared by dropwise adding a solution of 455 grams (3.3 moles) of 1-bromobutane in 700 mls of dry ether to a stirred slurry of 76.5 grams of magnesium (3.15 moles) in 600 mls of dry ether under nitrogen at reflux. The resulting solution is stirred at reflux for 30 minutes. A solution of 462 grams of 2,4,6-trimethyl-3-cyclohexenylcarboxaldehyde (3.0 moles) in 200 mls of ether is then added to the reaction mixture over a period of 1 hours at reflux under nitrogen. The resulting slurry is heated at reflux for 30 minutes and then cooled to 0° C. 1200 grams of 20% wt/wt sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 300 grams of isopropyl alcohol is added to the reaction mixture. Sulfuric acid (100 grams) is added slowly and the resulting solution is heated to reflux for 9 hours. At the end of this period the reaction mass is cooled. 500 ml of water and 200 ml of toluene is added thereto with stirring. The phases are allowed to separate and the aqueous phase is discarded. The organic phase is washed twice with H₂O, with sufficient sodium carbonate added to the second wash to adjust to pH to 7-8. Distillation of the organic layer affords 332 grams of product (b.p. 60°, 2.8 mm).

The NMR and IR spectra show fraction 10 of the distillation.

Figure 10:
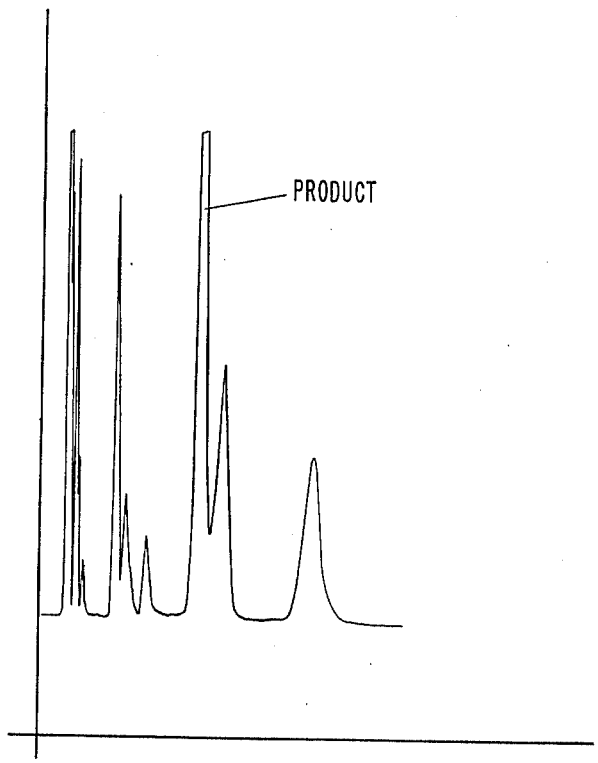
FIG. 10 is the GLC profile (after 8 hours of reflux) of the product produced according to Example IV, 3-n-butyl-1,5,8-trimethyl-2-oxabicyclo[2.2.2]octane.
Figure 11:
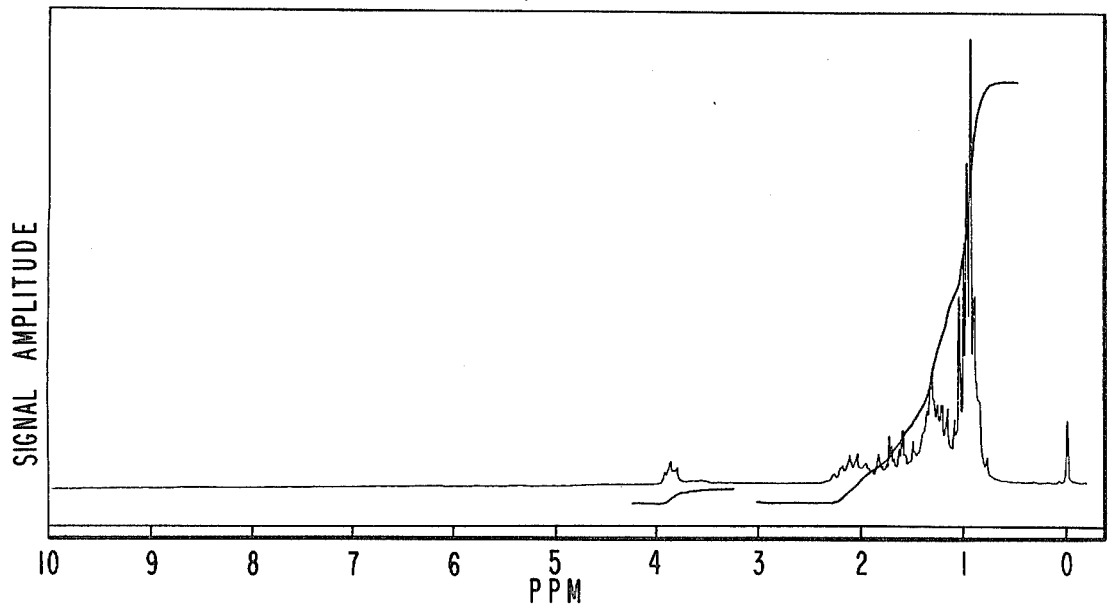
FIG. 11 is the NMR spectrum for fraction 10 of the distillate of the product produced according to Example IV.
Figure 12:
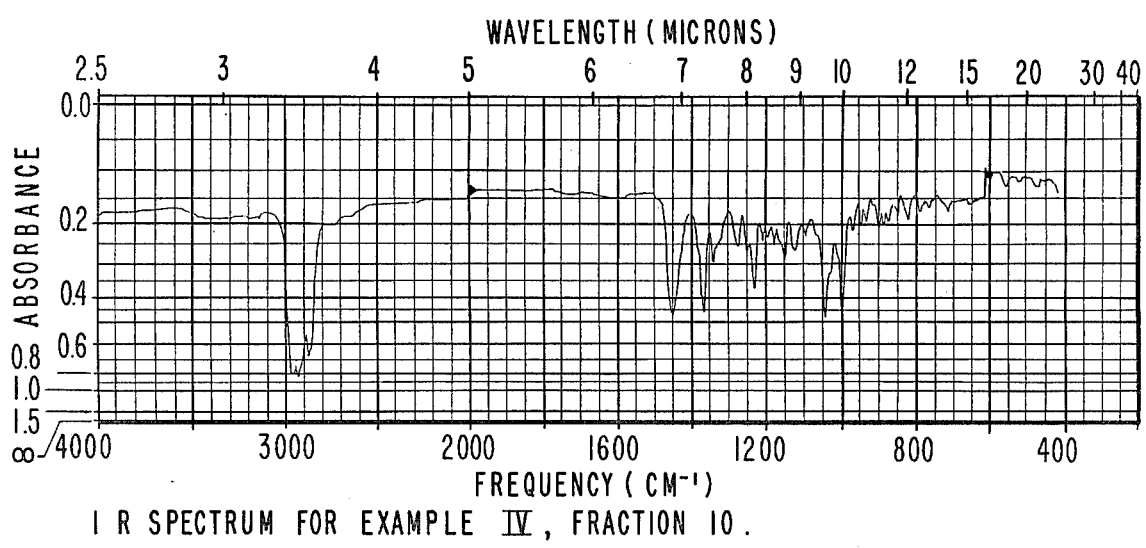
FIG. 12 is the infra-red spectrum for fraction 10 of the distillate of the product produced according to Example IV.

FIG. 10 is the GLC profile for the reaction product (Conditions: 180° isothermal; SE-30 column). The NMR spectrum for the resulting reaction product is set forth in FIG. 11. The infra-red spectrum for the resulting reaction product is set forth in FIG. 12.

EXAMPLE V

Preparation of
5-Ethyl-1,5-Dimethyl-3-n-Propyl-2-Oxabicyclo[2.2.2]Octane Reaction:

A solution of n-propylmagnesium bromide in ether is prepared by dropwise adding a solution of 197 grams (1.6 moles) of 1-bromopropane in 200 mls of dry ether to a stirred slurry of 38 grams of magnesium (1.55 moles) in 800 mls of dry ether under nitrogen at reflux. The resulting solution is stirred at reflux for 30 minutes. A solution of 250 grams of 2-ethyl-1,4-dimethyl-3-cyclohexenyl carboxaldehyde (1.51 moles) is then added to the reaction mixture over a period of 1 hour at reflux under nitrogen. The resulting slurry is heated at reflux for 30 minutes and then cooled to 0° C. 480 grams of 20% wt/wt sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 200 grams of isopropyl alcohol is added to the reaction mixture. Sulfuric acid (200 grams) is added slowly and the resulting solution is heated to reflux for 12 hours. At the end of this period the reaction mass is cooled. 500 ml of water and 200 ml of toluene is added thereto with stirring. The phases are allowed to separate and the aqueous phase is discarded. The organic phase is washed twice with H₂O, with sufficient sodium carbonate added to the second wash to adjust to pH to 7-8. Distillation of the organic layer affords 127 grams of product (b.p. 72° C., 2.1 mm).

The NMR and IR spectra show fraction 7 of the distillation.

Figure 13:
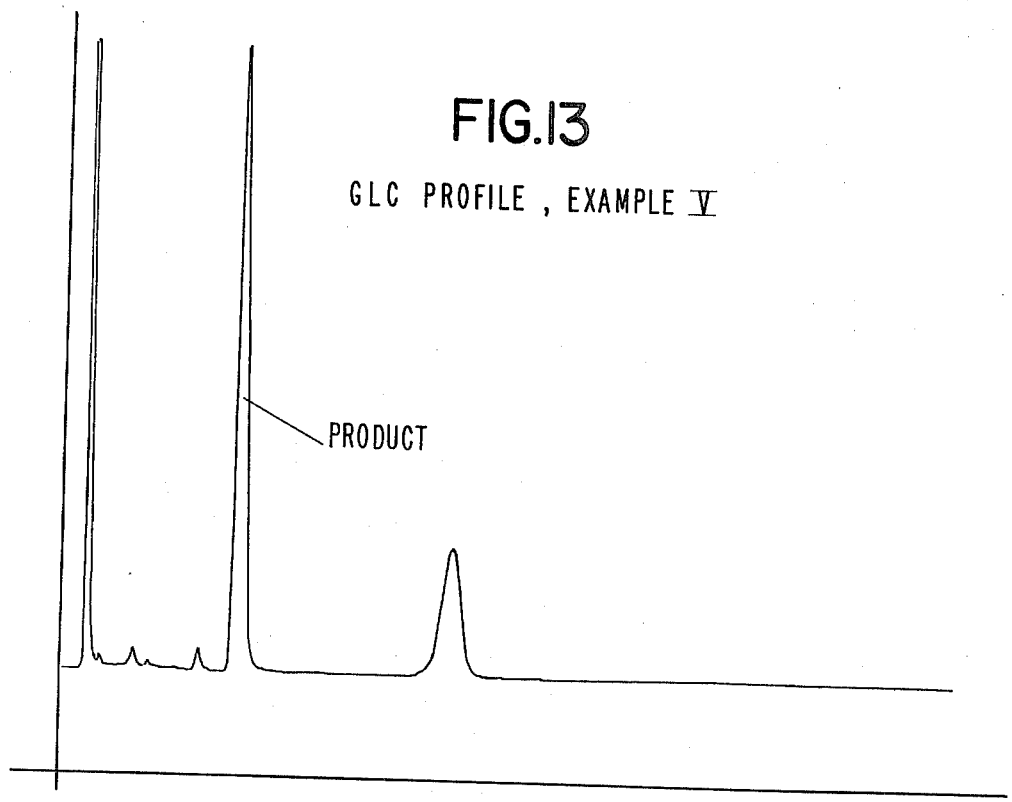
FIG. 13 is the GLC profile for the product produced according to Example V, 3-n-propyl-1,4-dimethyl-5-ethyl-2-oxabicyclo[2.2.2]octane.
Figure 14:
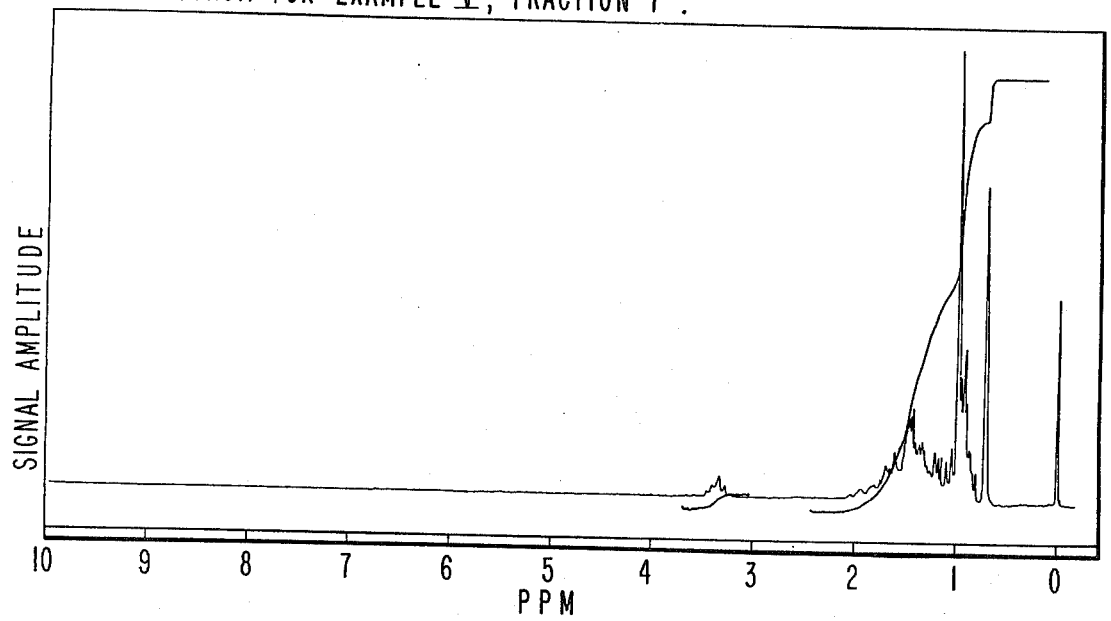
FIG. 14 is the NMR spectrum for fraction 7 of the distillate of the product produced according to Example V.
Figure 15:
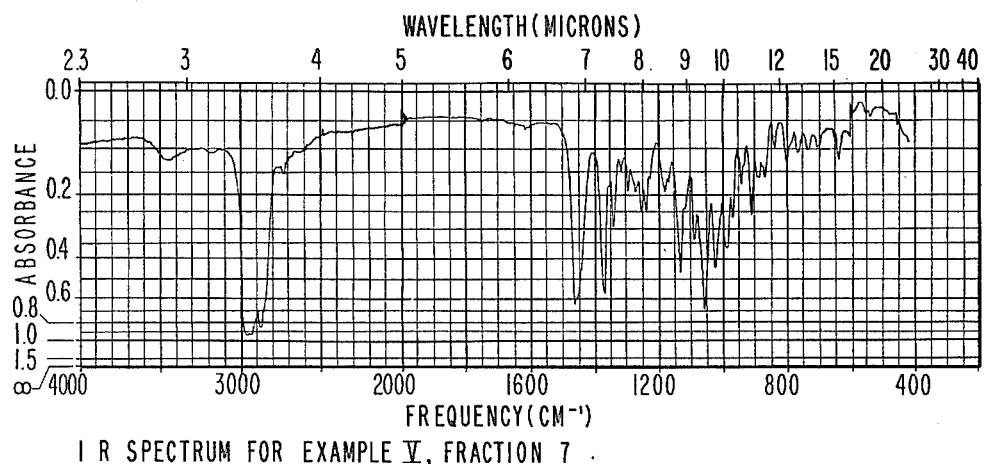
FIG. 15 is the infra-red spectrum for fraction 7 of the distillate of the product produced according to Example V.

FIG. 13 is the GLC profile for the reaction product (Conditions: 180° isothermal; SE-30 column). The NMR spectrum for the resulting reaction product is set forth in FIG. 14. The infra-red spectrum for the resulting reaction product is set forth in FIG. 15.

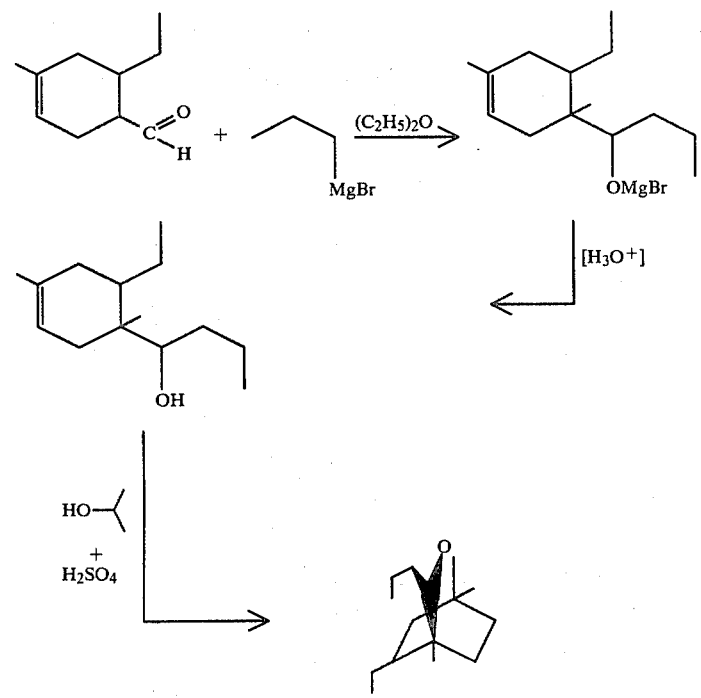

EXAMPLE VI

Preparation of
3-Methallyl-1,5,8-Trimethyl-2-Oxabicyclo[2.2.2]Octane
Reaction:

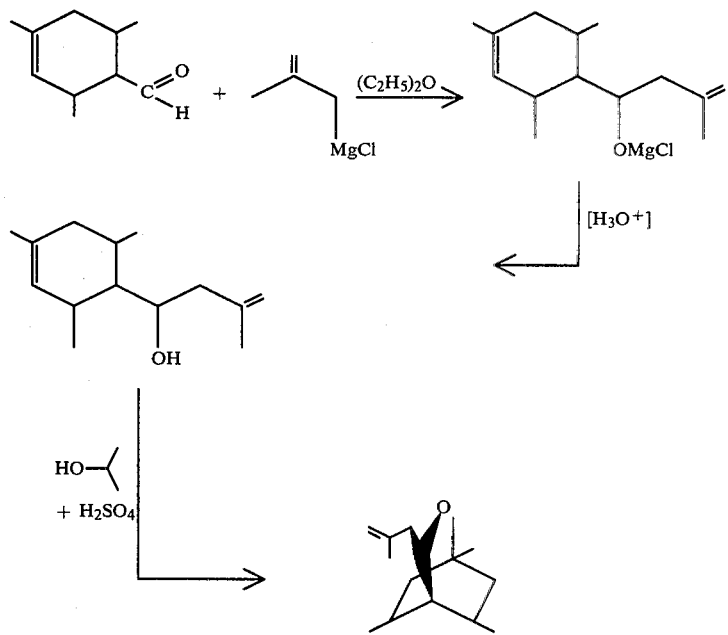

A solution of 319 grams (3.45 moles) of 3-chloro-2-methylpropene and 456 grams (3 moles) of 2,4,6-trimethyl-3-cyclohexenyl carboxaldehyde in 600 mls of ether is added dropwise to a slurry of 76.5 grams of magnesium (3.15 moles) in 600 mls of ether over a period of 1 hour at reflux under nitrogen. The resulting mixture is heated at reflux for 30 minutes and then cooled to 0° C. 1200 grams of 20% wt/wt sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 300 grams of isopropyl alcohol is added to the reaction mixture. Sulfuric acid (150 grams) is added slowly and the resulting solution is heated to reflux for 11 hours. At the end of this period the reaction mass is cooled. 500 m of water and 200 ml of toluene is added thereto with stirring. The phases are allowed to separate and the aqueous phase is discarded. The organic phase is washed twice with $H_2O$, with sufficient sodium carbonate added to the second wash to adjust to pH to 7–8. Distillation of the organic layer affords 196 grams of product (b.p. 79° C., 1 mm).

The NMR and IR spectra show fraction 8 of the distillation.

Figure 16:
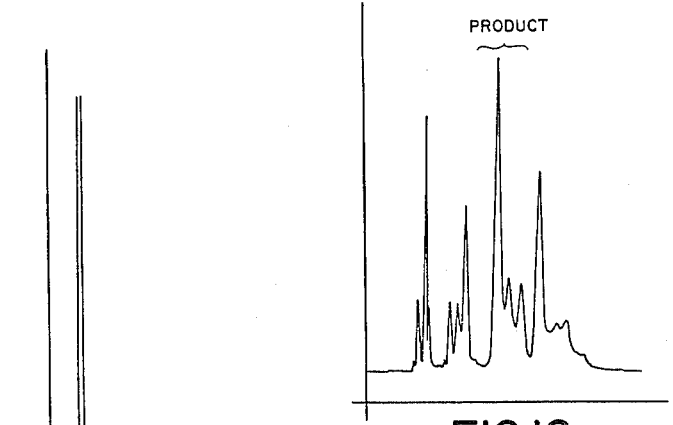
FIG. 16 is the GLC profile for the product produced according to Example VI, 3-(2'-methyl-2'-propenyl)-1,5,8-trimethyl-2-oxabicyclo[2.2.2]octane.
Figure 17:
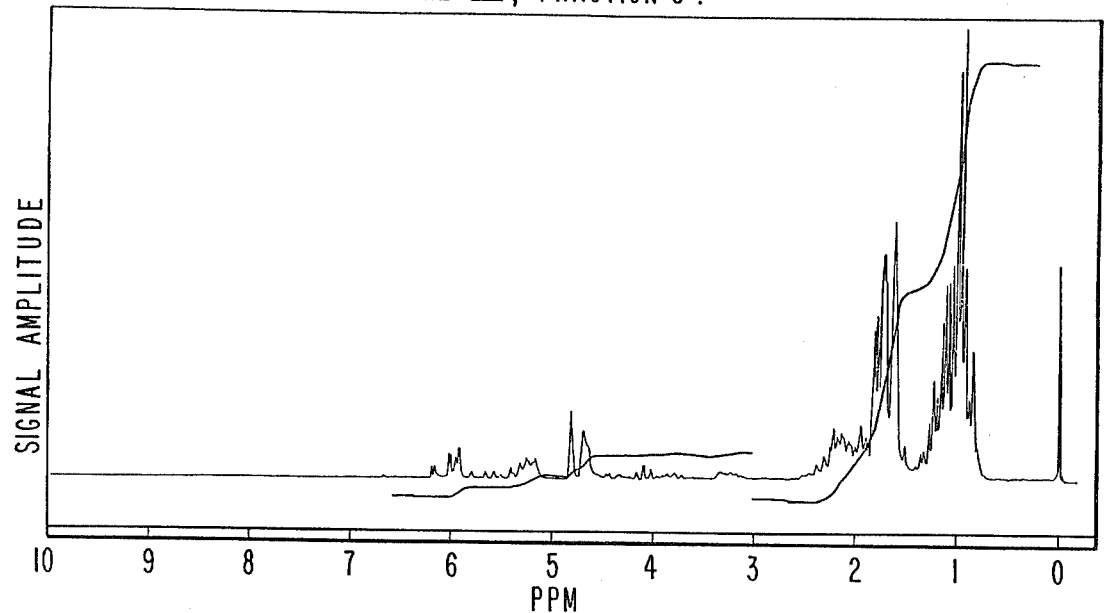
FIG. 17 is the NMR spectrum for fraction 8 of the distillate of the product produced according to Example VI.
Figure 18:
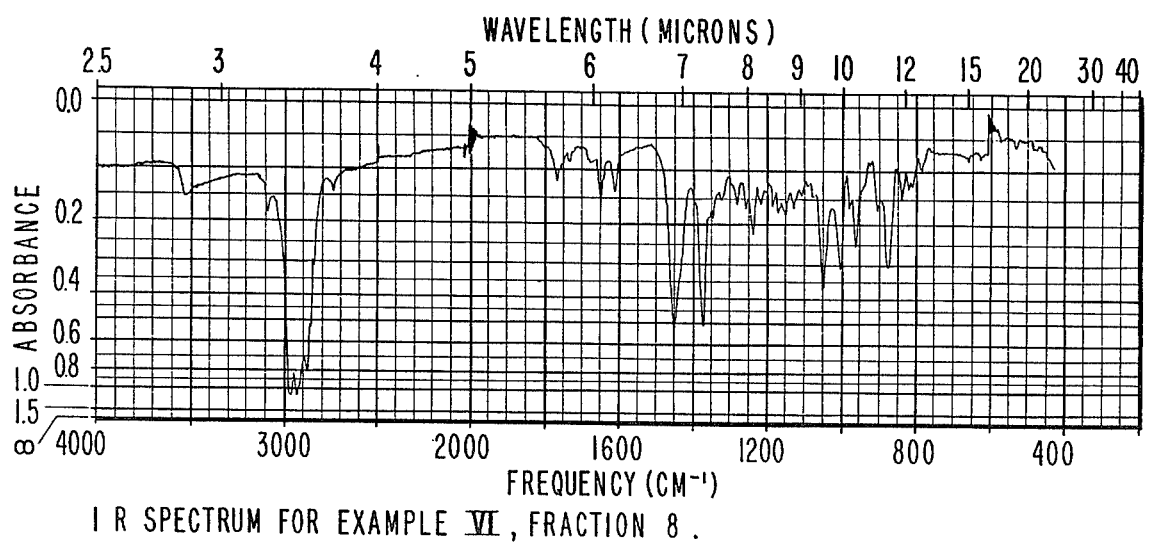
FIG. 18 is the infra-red spectrum for fraction 8 of the distillate of the product produced according to Example VI.

FIG. 16 is the GLC profile for the reaction product (Conditions: 180° isothermal; SE-30 column). The NMR spectrum for the resulting reaction product is set forth in FIG. 17. The infra-red spectrum for the resulting reaction product is set forth in FIG. 18.

EXAMPLE VII

Preparation of
3-Isopropyl-1,5,8-Trimethyl-2-Oxabicyclo[2.2.2]Octane
Reation:

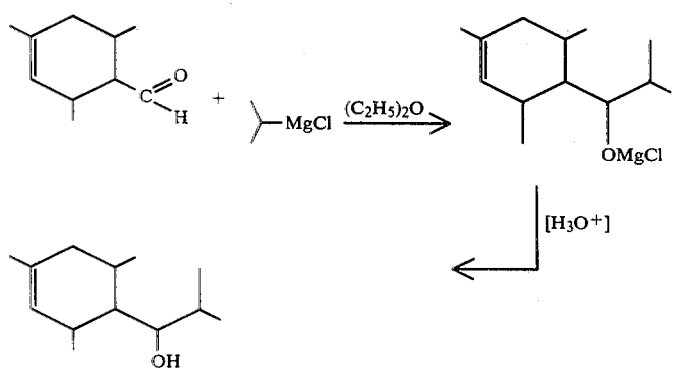

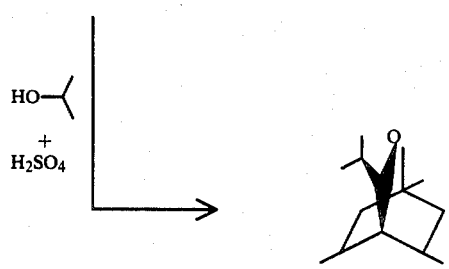

A solution of isopropylmagnesium chloride in ether is prepared by dropwise adding a solution of 269 grams (3.45 moles) of 2-chloropropane in 600 mls of dry ether to a stirred slurry of 76.5 grams of magnesium (3.15 mls) in 700 mls of dry ether under nitrogen at reflux. The resulting solution is stirred at reflux for 30 minutes. A solution of 444 grams of 2,4,6-trimethyl-3-cyclohexenyl carboxadelhyde (3 moles) in 200 mls of ether is then added to the reaction mixture over a period of 1 hour at reflux under nitrogen. The resulting slurry is heated at reflux for 30 minutes and then cooled to 0° C. 1300 mls of 10% aqueous hydrochloric acid is slowly added with external cooling over a 30 minute period. After the addition is complete, two clear layers appear. A distillation head is placed on the flask and ether is distilled from the reaction mixture at atmospheric pressure to a pot temperature of 90° C. 200 mls of isopropyl alcohol is added to the reaction mixture. Sulfuric acid (200 grams) is added slowly and the resulting solution is heated to reflux for 8 hours. At the end of this period the reaction mass is cooled. 500 ml of water and 200 ml of toluene is added thereto with stirring. The phases are allowed to separate and the aqueous phase is discarded. The organic phase is washed twice with $H_2O$, with sufficient sodium carbonate added to the second wash to adjust to pH to 7–8. Distillation of the organic layer affords 196 grams of product (b.p. 100°, 5 mm).

The NMR and IR spectra show fraction 5 of the distillation.

Figure 19:
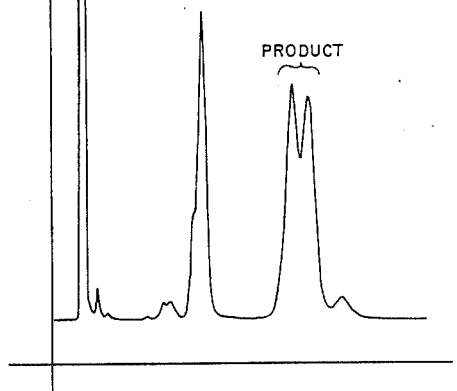
FIG. 19 is the GLC profile for the product produced according to Example VII, 3-i-propyl-1,3,5-trimethyl-2-oxabicyclo[2.2.2]octane.
Figure 20:
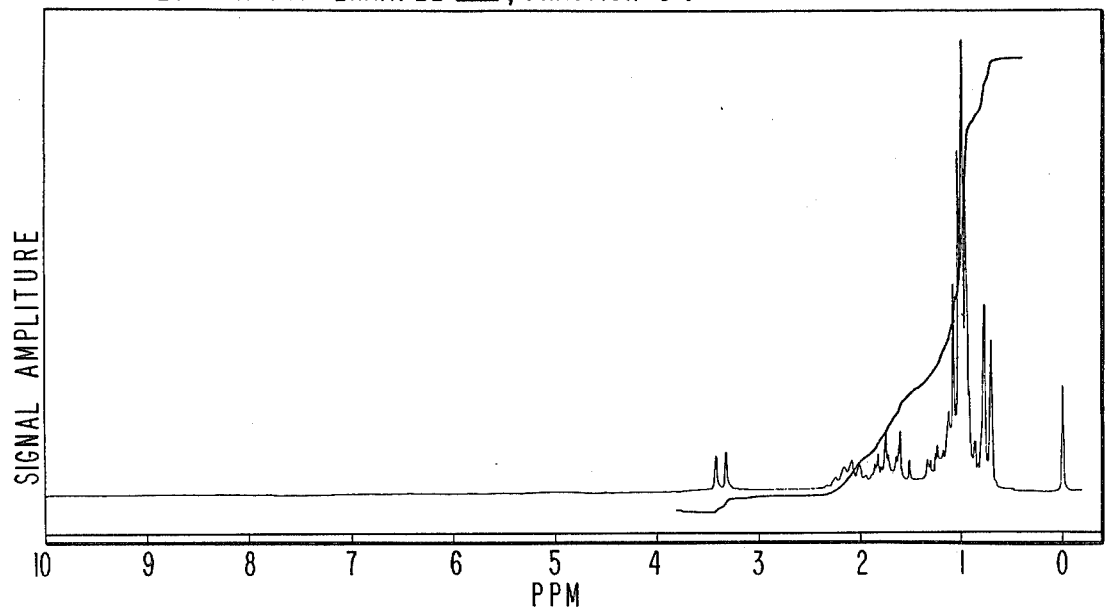
FIG. 20 is the NMR spectrum for fraction 5 of the distillate of the product produced according to Example VII.
Figure 21:
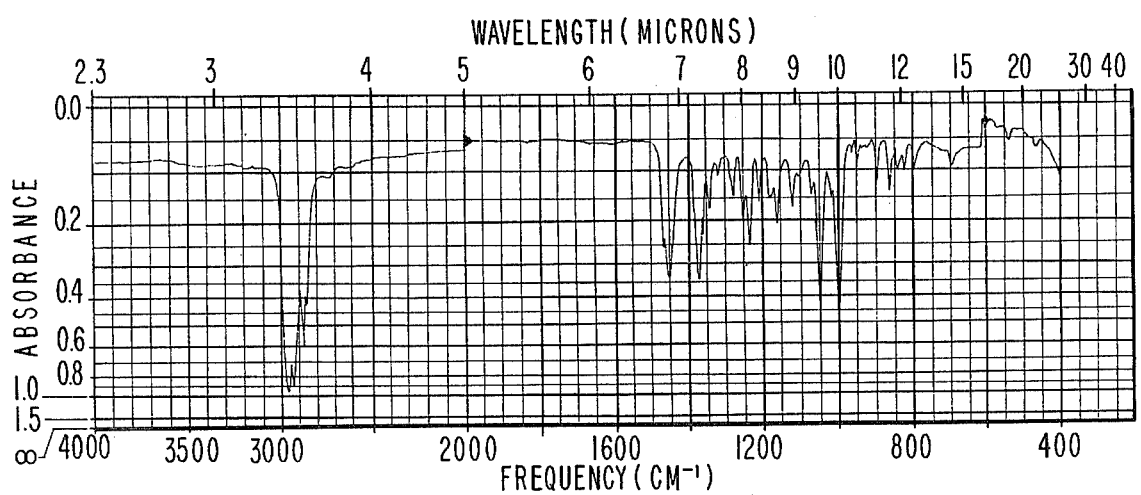
FIG. 21 is the infra-red spectrum for fraction 5 of the distillate of the product produced according to Example VII.

FIG. 19 is the GLC profile for the reaction product (Conditions: 180° isothermal; SE-30 column). The NMR spectrum for the resulting reaction product is set forth in FIG. 20. The infra-red spectrum for the resulting reaction product is set forth in FIG. 21.

EXAMPLE VIII

Blueberry Flavor Formulation

The following blueberry flavor formulation is prepared:

| Ingredients | Parts by Weight |
|---|---|
| Heliotropine | 2.0 |
| Terpinenol-4(10% in food grade ethanol) | 0.5 |
| Benzaldehyde | 1.5 |
| Phenyl acetaldehyde | 0.5 |
| Benzyl formate | 1.0 |
| Benzyl acetate | 2.0 |
| cis-3-Hexenylbenzoate (10% in food grade ethanol) | 0.5 |
| Methyl hexanoate | 2.0 |
| cis-3-Hexenol | 2.0 |
| Eucalyptol (1% in food grade ethanol) | 0.5 |
| Eugenol | 0.5 |
| Acetaldehyde (50% in food grade ethanol) | 8.0 |
| Ethyl benzoate | 1.0 |
| Ethyl butyrate | 25.0 |
| Ethyl acetate | 27.0 |
| Acetic acid (glacial) | 12.0 |
| 1,2-Propyleneglycol USP | 14.0 |

This basic blueberry flavor formulation is divided into two parts. To the first part nothing is added. To the second part is added 5% of 3-ethyl-1,5,8-trimethyl-2-oxabicyclo[2.2.2]octane prepared according to Example I. The blueberry flavor formulation with and without the added bicyclooctane derivative prepared according to Example I are compared at the rate of 20 ppm in water by a bench panel of experts (3 individuals) in the field of foodstuff flavors. The flavors with the added bicyclooctane derivative have a more juicy character and more of the piney notes found in wild blueberries both in aroma and taste. In addition, the aroma characteristics are substantially stronger in the formulation which contains the bicyclooctane derivative produced according to Example I when compared with the formulation not containing said bicyclooctane derivative.

Therefore, the flavor with the bicyclooctane derivative, the 3-ethyl-1,5,8-trimethyl-2-oxabicyclo[2.2.2]octane is unanimously preferred by all three tasters as having a more natural-like natural blueberry characteristic.

EXAMPLE IX

CLOVE BUD OIL FORMULATION

The following clove bud oil formulation is prepared:

| Ingredients | Parts by Weight |
|---|---|
| Vanillin | 20 |
| Caryophyllene | 80 |
| Guaiacol | 1 |
| Cuminaldehyde | 10 |
| 5-Methylfurfural | 50 |
| Eugenol | 830 |

The foregoing formulation is divided into two parts. To the first part nothing is added. To the second part at the rate of 5%, 3-isopropyl-1,5,8-trimethyl-2-oxabicyclo[2.2.2]octane prepared according to Example VII is added. Both flavors, with and without the additional bicyclooctane derivative are compared at the rate of 10 ppm in water and evaluated by a bench panel of experts. All the members of this bench panel state that the clove bud oil formulation containing the bicyclooctane derivative prepared according to Example VII has more of the notes present in natural clove bud oil; woody-rich, floral-sweet, spicey-pungent notes. In summary, the oil with the bicyclooctane derivative the 3-isopropyl-1,5,8-trimethyl-2-oxabicyclo[2.2.2]octane is more natural.

Therefore, all members of the bench panel prefer, unanimously, the clove bud oil formulation containing the additional 3-isopropyl-1,5,8-trimethyl-2-oxabicyclo[2.2.2]octane prepared according to Example VII.

EXAMPLE X

A. Powder Flavor Formulation

20 Grams of the flavor composition of Example VIII is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
| --- | --- |
| Liquid Blueberry Flavor Composition of Example VIII | 20 |
| Propylene glycol | 9 |
| Cab-O-Sil ® M-5 (Brand of Silica produced by the Cabot Corporation of 125 High Street, Boston, Mass. 02110; Physical Properties: Surface Area: 200 m$^2$/gm Nominal particle size: 0.012 microns Density: 2.3 lbs./cu.ft.) | 5.00 |

The Cab-O-Sil is dispersed in the liquid blueberry flavor composition of Example VIII with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example VIII is added to the solution which is then homogenized to form an emulsion having particle size typically in the range of 2-5 microns. This material is kept at 120° F. under which conditions the gelatin will not jell.

Coacervation is induced by adding slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XII

Chewing Gum

100 Parts by weight of chicle are mixed with 4 parts by weight of the flavor prepared in accordance with Example X. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting blueberry flavor.

EXAMPLE VIII

Chewing Gum

100 Parts by weight of chicle are mixed with 18 parts by weight of the flavor prepared in accordance with Example XI. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting blueberry flavor.

EXAMPLE XIV

A. Powder Flavor Formulation

20 Grams of the flavor composition of Example IX is emulsified in a solution containing 300 gm gum acacia and 700 gm water. The emulsion is spray dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
| --- | --- |
| Liquid Clove Bud Flavor Composition of Example IX | 20 |
| Propylene glycol | 9 |
| Cab-O-Sil ® M-5 (Brand of Silica produced by the Cabot Corporation of 125 High Street, Boston, Mass. 02110; Physical Properties: Surface Area: 200 m$^2$/gm Nominal particle size: 0.012 microns Density: 2.3 lbs/cu.ft.) | 5.00 |

The Cab-O-Sil is dispersed in the liquid clove bud flavor composition of Example IX with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XV

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example IX is added to the solution which is then homogenized to form an emulsion having particle size typically in the range of 2-5 microns. This material is kept at 120° F. under which conditions the gelatin will not jell.

Coacervation is induced by adding slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XVI

Chewing Gum

100 Parts by weight of chicle are mixed with 4 parts by weight of the flavor prepared in accordance with Example XIV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting clove bud flavor.

EXAMPLE XVII

Chewing Gum

100 Parts by weight of chicle are mixed with 18 parts by weight of the flavor prepared in accordance with Example XV. 300 Parts of sucrose and 100 parts of corn syrup are then added. Mixing is effected in a ribbon blender with jacketed side walls of the type manufactured by the Baker Perkins. Co.

The resultant chewing gum blend is then manufactured into strips 1 inch in width and 0.1 inches in thickness. The strips are cut into lengths of 3 inches each. On chewing, the chewing gum has a pleasant, long lasting clove bud flavor.

EXAMPLE XVIII

Toothpaste Formulation

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalsium Phosphate (Dihydrate) |
| Group "C" | |
| 2.000 | Sodium N-Lauroyl Sarcosinate (foaming agent) |
| Group "D" | |
| 1.200 | Flavor Material of Example XIV |
| 100.00 TOTAL | |

PROCEDURE:
1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant clove bud flavor, of constant strong intensity throughout said procedure (1–1.5 minutes).

EXAMPLE XIX

Chewable Vitamin Tablets

The flavor material produced according to the process of Example XIV is added to a Chewable Vitamin Tablet. Formulation at a rate of 10 gm/Kg which Chewable Vitamin Tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.11 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example XIV | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 gm dry Vitamin A Acetate and 0.6 gm Vitamin D are then added as beadlets. The entire blend is then compressed using concave punches at 0.5 gm each.

Chewing of the resultant tablets yields a pleasant, long-lasting, consistently strong clove bud flavor with lime nuances for a period of 12 minutes.

EXAMPLE XX

Chewing Tobacco

On 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| 3-Isopropyl-1,5,8-Trimethyl-2-Oxabicyclo[2.2.2]Octane Prepared According to Example VII | 0.04 |

The resultant product is redried to a moisture content of 20%. On chewing, this tobacco has an excellent substantially consistent, long-lasting clove bud nuance in conjunction with the tobacco notes.

EXAMPLE XXI

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 3-isopropyl-1,5,8-trimethyl-2-oxabicylco[2.2.2]octane produced according to Example VII at 100 ppm per cigarette. Another one-third of these model cigarettes are treated in the filter with 3-isopropyl-1,5,8-trimethyl-2-oxabicyclo[2.2.2]octane produced according to Example VII at the rate of $2 \times 10^{-5}$ gm. When evaluated by paired comparison, the cigarettes treated both in the tobacco and in the filter with the 3-isopropyl-1,5,8-trimethyl-2-oxabicyclo[2.2.2]octane are found, in smoke flavor, to be more tobacco-like with enhanced clove bud nuances.

EXAMPLE XXII

The following is a description of a preferred embodiment of the invention as carried out using a process wherein minute capsules having a diameter in the range of 50 up to 500 microns were added to a wet web of reconstituted tobacco (weight ratio of dry web to dry capsules=1:0.04. The capsules and binder materials (weight ratio of dry capsule to dry binder=1:0.1) when placed among the tobacco fibers, wet them and entangle with them and clothe them, thus in effect securing and binding the capsules against migration through the sheet, thereby forming a subsident stratum. The majority of binder and associated capsules are caught in the sheet. Substantially no capsules migrate through the sheet. When the wet tobacco web is dried, the binder shrinks by loss of solvent, leaving the dried polymeric binder material, and the capsules remain in place relatively with respect to sheet thickness. The sheets containing the capsules are then shredded and used in producing smoking articles such as cigarettes. Such cigarettes are formed using a wrapper, containing a fill of tobacco extending from one end of the wrapper to the other, and intimately admixed with the tobacco, a plurality of microcapsules each comprising an aromatic volatile synthetic clove oil flavorant. The capusles are homogeneously spaced in contiguous relationship with the tobacco such that as the burning front of the tobacco advances the length of the tobacco article, a concomitant elevation of temperature initiates consecutive rupture of the capsules (1) releasing the voltile synthetic clove oil-containing material which emanates with smoke from the smoking article into the smoker's mouth and (2) yielding crackling sound audible to the human ear.

Tragacanth gum solution and starch solution were prepared in the following manner:

PART A

Concentrated Tragacanth Gum Solution (binder)

4.5 pounds of dry tragacanth gum powder was stirred into 50 gallons of water, using a suitable mixer. Five minutes after all the powder had been added, the mixer was turned off. The trgacanth gum solution was allowed to sit for 2 hours, and then the mixer was turned on for 5 minutes. Sitting for 2 additional hours, enabled the tragacanth gum to hydrate. After five minutes, the mixer was turned off, and the 55 gallon drum was covered. Just prior to combining the tragacanth gum solution and the capsular slurry, 50 gallons of tragacanth gum solution was diluted with water to 3 percent tragacanth gum on a solids basis.

PART B

Starch Solution

The hydrolyzed starch solution was prepared by heating a slurry of the starch at 195 degrees Fahrenheit for a minimum of 15 minutes to provide a 1 percent by weight, starch-in-water solution.

Capsules slurries were prepared in the following manner:

PART C

Preparation of Synthetic Clove Oil

| Ingredient | Percentage |
| --- | --- |
| alpha Caryophyllene | 2.0 |
| beta Caryophyllene | 2.0 |
| gamma Caryophyllene | 5.0 |
| Furfural | 75.0 |
| Eugenyl Acetate | 5.0 |
| Acetyl Eugenols | 5.9 |
| 3-Isopropyl-1,5,8-Trimethyl-2-Oxabicyclo[2.2.2]Octane Prepared According to Example VII | 5.0 |

PART D

Preparation of Capsular Slurry-Encapsulation of Synthetic Cove Oil

Ten grams of gum arabic were dissolved at room temperature in 220 grams of dionized water. The mixture was agitated until the gum arabic was fully dissolved. In a separate 240 milliliter Erlenmeyer Flask, 10.0 grams of modified gelatin was mixed with 220.0 grams of deionized water. The gelatin was allowed to tumefy at room temperature and also then warmed in a water bath to about 40° C. with stirring so that the gelatin was dissolved.

The gelatin solution and the gum arabic solution were poured into a beaker equipped with a stirrer. A flocculence indicating the precipitation of the gelatin was noted. The temperature of the mixture was decreased to 35° C. The speed of the stirrer was adjusted so that it was turning only enough to keep the phases mixed. The pH of the mixture was 4.50.

Into the beaker containing the mixture of gum arabic and gelatin was poured 118.0 grams of synthetic clove oil as prepared in part C. The speed of the stirrer was then adjusted to mix the colloids and the oil. The oil separated into droplets. Two drops of octyl alcohol were added to prevent foaming. The progress of the coacervation was monitored by means of microscopic examination.

The temperature of the mixture was lowered to room temperature e.g., 24° C. At the higher temperature of 31° C. colloid deposition was observed on the oil droplets. At 24° C. little colloid could be observed in aqueous portions of the mixture. Deposition had ceased. Stirring was continued for 30 minutes, whereupon the reaction mixture was cooled on an ice bath to 4° C. The reaction mixture was maintained at this temperature for 200 minutes. (When hardening was desired, 1.0 milliters of a 25 percent glutaraldehyde in water per gram of gelatin is added.)

The internal phase of the capsules thus formed was approximately 80-90 percent of the total weight of the capsules.

The capsules thus produced had diameters in the range of from 50 up to 500 microns. They were coated with the binder onto a tobacco sheet material which was shredded and used as a fill in the manufacture of a smoking article.

PART E

Variation of the Encapsulation of Synthetic Clove Oil

A variation of the encapsulation procedure set forth immmediately supra is shown below:

The solution of gum arabic was warmed to 38° C., placed in a Waring blender and stirred. The clove oil prepared in part C was added gradually while the speed of the blender was being increased until the size of the clove oil droplets was approximately 50-500 microns. The mixture thus formed was poured into a 1,000 milliliter beaker containing gelatin, also at 38° C., and was stirred thoroughly. The temperature was then allowed to drop to room temperature and then further decreased to a temperature of 4° C. to 10° C. by means of an ice bath.

It is evident that the tobacco film or filaments can be made from various types and combinations of tobacco. For instance, the tobacco sheet material can be made from relatively expensive tobacco such as Latakia in which it is highly desirous to use all waste because of the high price thereof. So, also, it may be formed of Burley or one or more scrap or waste cigarette type tobaccos and incorporated in accordance with a particular cigarette manufacture's formula as if it were natural cigarette tobacco leaves. Any desired formula can thus be maintained in accordance with the demands of a manufacturer's particular brand using one or more types of natural shredded tobacco leaves and admixed desired quantities of shredded capsule containing tobacco film material or filaments, either as a blending or flavoring medium or both or for purposes of bulking.

In the case of the manufacture of cigarettes, according to the present invention, tobacco films are shredded into strands or the film is formed directly into filaments substantially the width of the strands of natural shredded tobacco and of any desired length. In the case of cigars, the capsule containing films are used in large pieces much as long filler tobacco in forming long filter cigars. In all cases the shredded films or filaments or film used in cigarettes and cigars can be handled either manually or by machine in the same mammer as natural shredded tobacco leaves or whole leaves or portions thereof. The amount of shredded capsule-containing reconstituted tobacco or pieces of this material employed in a particular blend in cigarettes or cigars, respectively, will vary according to types of tobacco used in the sheet material and the requirements of a particular manufacture.

EXAMPLE XXIII

The following is a description of another preferred embodiment of the invention as carried out using a process wherein an aqueous slurry of minute capsules having diameters in the range of 50-5000 microns were admixed with shredded natural leaf tobacco.

The capsules and binder materials, when placed among the tobacco shreds, wet them and entangle with them thus securing the capsules against disengaging from the tobacco shreds and separating from a smoking article produced therefrom. Such cigarettes are formed using a wrapper, containing a fill of tobacco extending from one end of the wrapper to the other, and ultimately admixed with the tobacco, a plurality of microcapsules each comprising an aromatic volatile synthetic clove oil flavorant. The capsules are homogeneously spaced in contiguous relationship with the tobacco such that as the burning front of the tobacco advances the length of the tobacco article, a concomitant elevation of temperature initiates consecutive rupture of the capsules (1) releasing the volatile synthetic clove oil-containing material which emanates with smoke from the smoking article into the smoker's mouth and (2) yielding a crackling smound audilbe to the human ear.

PART C

Encapsulation of Synthetic Clove Oil 3750 cubic centimeters of synthetic clove oil produced by the procedure of part C of Example XXII and 315 grams of gelatin in 6,950 cubic centimeters of water was stirred at 200 r.p.m. (six blade axial flow agitator with four evenly spaced baffles) until the particle size was in the range of 50 microns to 500 microns (45-minute stirring). A solution of 315 grams of gum arabic in 6,950 cubic centimeters of deionized water was then added. The pH of the resulting mixture was adjusted to 4.5 by the addition of a 10 percent solution of sodium hydroxide in water. The mixture was slowly cooled on a water bath to a temperature of 38° C. 151.5 cubic centimeters of a 25 percent solution of glutaraldehyde in water was added. 7.7 grams of sodium benzoate was added. The resulting capsule slurry was stirred for 30 minutes and then filtered using a 20 mesh sieve.

The capsules were then suspended in a mixture of 3 parts gum tragacanth and 17 parts water and the resulting suspension was sprayed onto shredded natural leaf tobacco (using a two fluid pnematic atomizing nozzle; ¼ J.A.U.SS manufactured by the Spraying Systems, Inc.) The weight ratio of dry capsule to dry shredded tobacco was 0.04:1. The product was used as a fill for cigarettes which, when smoked, released a volatile clove oil flavor and aroma, and yielded a crackling sound audible to the human ear.

PART B

Alternative Procedure for Encapsulation of Clove Oil Slurry 10.0 parts by weight of spray dried gum arabic was dissolved in 220 parts by weight of deionized water in a beaker equipped with a stirrer. In a separate 250 milliliter Erlenmeyer flask, 10.0 parts by weight of gelatin was dissolved in a 220 parts by weight of deionized water.

35.4 parts by weight of beta,gamma-dimethyl-gamma-butyrolactone produced by the process of example III of Canadian Pat. No. 805,934 and 82.6 parts by weight of synthetic clove oil prepared by the process of part C of example XXII were added to the gum arabic solution. The temperature of the mixture was adjusted to 33° C. Thereafter, the solution of gelatin was added with rapid stirring. The reaction mixture was cooled to a temperature of 10° C. on an ice bath while continuously stirred. The mixture was stirred for one hour at 10° C. Thereafter, 5.0 parts by weight of a 25 percent solution of glutaraldehyde in water was added to the reaction mass.

The reactant mass was stirred at 10° C. for 8 hours. The resulting capsules had a spherical diameter in the range of from 50 up to 500 microns. The capsules thus formed were not dried but were immediately sprayed onto shredded tobacco. The resulting product was rolled into a cigarette. The cigarette when smoked released a volatile cove oil flavor and aroma and also yielded a crackling sound audilbe to the human ear.

EXAMPLE XXIV

Sandal Cologne Formulation

The following "Sandal Cologne" perfume formulation is prepared:

| Ingredients | Parts by Weight |
| --- | --- |
| Trimethyl-(2,2,3-norbornyl-5) 3-cyclohexanol-1 | 100 |
| 1',2',3',4',5',6',7',8'-octahydro-2',3',8',8'-tetramethyl-2'-aceto-naphthone isomer mixture produced according to the process of Example VII of Application for U.S. Letters Pat. No. 434,948 filed on January 21, 1974 | 50 |
| 2,5,5-trimethyl acetyl cycloheptane produced according to Example I of U.S. Pat. Application No. 349,180 filed on April 9, 1973 | 10 |
| Eugenol (10% sol. in diethyl phthalate) | 5 |
| Borneol (1% sol. in ethyl alcohol) | 2 |
| Cedrenal (A tricyclic sesquiterpinic aldehyde derived from cedrene, having the structure:<br><br>produced according to the process of U.S. Pat. Application No. 260,537 filed on June 7, 1972 (corresponding to published Dutch Appln. 7307849 laid open for public inspection on December 11, 1973) | 15 |
| 2,2-Dimethyl-3-(2-(2,3-dimethyl-tricyclo-(2,2,1,0$^{2,6}$)-hept-3-yl) ethyl)-oxirane having the structure: | 50 |
| 3-n-Butyl-1,5,8-trimethyl-2-oxabicyclo [2.2.2] octane prepared according to Example IV | 12 |

The 3-n-butyl-1,5,8-trimethyl-2-oxabicyclo[2.2.2]octane imparts a dry wood leathery aroma profile which is an important odor factor in East Indian Sandalwood.

EXAMPLE XXV

Preparation of a Cosmetic Powder Composition

A cosmetic powder is prepared by mixing in a ball mill, 100 g of talcum powder with 0.25 g of the perfume composition prepared according to Example IV. It has an excellent dry woody, leathery, sandalwood aroma.

EXAMPLE XXVI

Perfumed Liquid Detergent

Concentrated liquid detergents (Lysine salt of n-dodecylbenzene sulfonic acid as more specifically described in U.S. Pat. No. 3,948,818 issued on Apr. 6, 1976) with dry woody, leathery, sandalwood aroma nuances are prepared containing 0.10%, 0.15% and 0.20% of the fragrance prepared according to Example XXIV. They are prepared by adding and homogeneously mixing the appropriate quantity of fragrance formulation prepared according to Example XXIV in the liquid detergents. The detergents all possess excellent dry woody, leathery, sandalwood aromas, the intensity increasing with greater concentrations of perfume composition of Example XXIV.

EXAMPLE XXVII

Preparation of a Cologne and Handkerchief Perfume

The composition prepared according to Example XXIV is incorporated into a cologne at concentrations of 2.0%, 2.5%, 3.0%, 3.5%, 4.0%, 4.5%, and 5.0% in 85% aqueous food grade ethanol; and into a handkerchief perfume at concentrations of 15%, 20%, 25%, and 30% (in 95% aqueous food grade ethanol). A distinctive and definite dry woody, leathery, sandalwood aroma is imparted to the cologne and to the handkerchief perfume at all levels indicated above.

EXAMPLE XXVIII

Preparation of Soap Composition

One hundred grams of soap chips are mixed with one gram of each of the formulations of Example XXIV until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest dry woody, leathery, sandalwood aromas.

EXAMPLE XXIX

Preparation of a Solid Detergent Composition

A detergent is prepared from the following ingredients according to Example I of Canadian Pat. No. 1,007,948:

|  | Percent by Weight |
|---|---|
| "Neodol 45-11" (a $C_{14}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.15 grams of each of the sandal colgne perfume of Example XXIV. Each of the detergent samples has an excellent dry woody, leathery, sandalwood aroma being imparted as a result of using the oxabicyclo[2.2.2]octanes prepared according to Example IV.

EXAMPLE XXX

Preparation of a Cosmetic Powder Composition

A cosmetic powder is prepared by admixing in a ball mill, 100 g of talcum powder with 0.25 g of 3-n-butyl-1,5,8-trimethyl-2-oxabicyclo[2.2.2]octane prepared according to Example IV. The resulting cosmetic powder has an excellent dry woody, leathery, sandalwood aroma.

EXAMPLE XXXI

Perfumed Liquid Detergent

Concentrated liquid detergents (Lysine salt of n-dodecylbenzene sulfonic acid as more specifically described in U.S. Pat. No. 3,948,818 issued on Apr. 6, 1976) with dry woody, leathery, sandalwood aroma are prepared containing 0.1%, 0.15%, 0.2%, and 0.25% of 3-n-butyl-1,5,8-trimethyl-2-oxabicyclo[2.2.2]octane prepared according to Example IV. They are prepared by adding and homogeneously mixing the appropriate quantity of 3-n-butyl-1,5,8-trimethyl-2-oxabicyclo[2.2.2]octane in the liquid detergent. The detergents all possess dry woody, leathery, sandalwood aromas, the intensity of each of the foregoing characteristics increasing with greater concentrations of the 3-n-butyl-1,5,8-trimethyl-2-oxabicyclo[2.2.2]octane.

EXAMPLE XXXII

Preparation of Cologne and Handkerchief Perfume 3-n-butyl-1,5,8-trimethyl-2-oxibicyclo[2.2.2]octane prepared according to Example IV is incorporated into colognes at concentrations of 2.0%, 2.5%, 3.0%, 3.5%, 4.0%, and 4.5% in 85% aqueous food grade ethanol; and into handkerchief perfumes at concentrations of 15%, 20%, 25% and 30% (in 95% aqueous ethanol). Distinctive dry woody, leathery, sandalwood aroma nuances are imparted to the colognes and to the handkerchief perfumes at the various above levels.

EXAMPLE XXXIII

Utilizing the procedure of Example I of column 15 of U.S. Pat. No. 3,632,396, a nonwoven cloth substrate useful as a dryer-added fabric-softening article a manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of 3-n-butyl-1,5,8-trimethyl-2-oxabicyclo[2.2.2]octane (which gives rise to a dry woody, leathery, sandalwood aroma) derivative or cyclohexyl alkyl or alkenyl carbinol or ester thereof of our invention as set forth in the Table I below and giving rise to the aroma nuances as set forth in said Table I below:

TABLE I

| NAME OF COMPOUND | FRAGRANCE CHARACTERISTICS |
|---|---|
| 1,5-Dimethyl-3-isopropyl-2-oxabicyclo [2. 2. 2]octane | A green, minty, herbaceous (rosemary) aroma with a cooling effect. |
| 3-allyl-1-methyl-2-oxabicyclo[2. 2. 2] octane | A minty, eucalyptol-like, herbaceous (garden mint, thyme), buchu-like aroma with caraway-like nuances. |
| 3-n-butyl-2,5-dimethyl-2-oxabicyclo[2. 2. 2] octane | A green, spicey, carvone-like aroma. |
| 1,5-dimethyl-3-n-propyl-2-oxabicyclo[2. 2. 2] octane | A herbaceous, minty (garden mint) aroma with basil, thyme and caraway nuances. |
| 1,5-dimethyl-3-n-pentyl-2-oxabicyclo[2. 2. 2] octane | An oily, green, herbaceous (wet lettuce) aroma. |
| α-allyl-4-methyl-3-cyclohexenemethanol | A sweet, anise, carvone-like and minty aroma. |
| 2,4-dimethyl-α-allyl-3-cyclohexenemethanol | A sweet, anisic, citrus aroma with minty, peppery, and geranium-like undertones. |
| α-allyl-4-methyl-3-cyclohexene-1-methanol | A sweet, fruity, herbaceous, floral aroma with carvone- |

TABLE I-continued

| NAME OF COMPOUND | FRAGRANCE CHARACTERISTICS |
| --- | --- |
| acetate | like and geranyl acetate-like nuances. |
| 4,6-dimethyl-α-allyl-3-cyclohexenemethanol | A sweet, herbaceous, fruity aroma with basil and blueberry-like undertones. |
| α-allyl-4,6-dimethyl-3-cyclohexene-1-methanol acetate | A green, fruity, anisic, woody aroma. |
| | A green, floral, minty, lemonly aroma. |

A fabric-softening composition prepared as set forth above having the above aroma characteristics essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aroma as set forth above is imparted in a pleasant manner to the head space in the dryer on operation thereof using said dryer added fabric softening nonwoven fabric.

What is claimed is:

1. The compound having the structure:

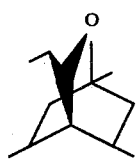

2. The compound having the structure:

3. The compound having the structure:

4. The compound having the structure:

5. The compound having the structure:

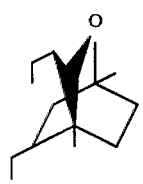

6. The compound having the structure:

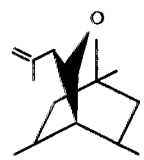

7. The compound having the structure:

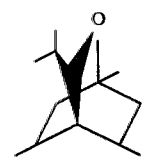

* * * * *